(12) United States Patent
Uehara

(10) Patent No.: US 10,814,166 B1
(45) Date of Patent: Oct. 27, 2020

(54) SYSTEM AND METHOD FOR DEVELOPING CORE MUSCLE USAGE EMPLOYING MUSIC

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 433 days.

(21) Appl. No.: 15/142,558

(22) Filed: Apr. 29, 2016

Related U.S. Application Data

(63) Continuation-in-part of application No. 14/789,136, filed on Jul. 1, 2015, now Pat. No. 9,706,962, which is a continuation-in-part of application No. 14/132,808, filed on Dec. 18, 2013, now Pat. No. 9,226,706.

(60) Provisional application No. 62/154,626, filed on Apr. 29, 2015, provisional application No. 61/739,160, filed on Dec. 19, 2012.

(51) Int. Cl.
*A61B 5/00* (2006.01)
*A63B 24/00* (2006.01)
*A61B 5/11* (2006.01)

(52) U.S. Cl.
CPC ......... *A63B 24/0062* (2013.01); *A61B 5/1107* (2013.01); *A61B 5/1108* (2013.01)

(58) Field of Classification Search
CPC ....... A63B 24/0062; A63B 24/00; A61B 5/11; A61B 5/1107; A61B 5/1108
See application file for complete search history.

(56) References Cited

U.S. PATENT DOCUMENTS

| 5,474,083 A | * | 12/1995 | Church | A61B 5/0488 600/546 |
| 5,871,499 A | * | 2/1999 | Hahn | A61B 17/42 600/588 |
| 6,264,582 B1 | * | 7/2001 | Remes | A63B 23/20 482/8 |
| 2013/0116601 A1 | * | 5/2013 | Tomazic | A61B 5/224 600/595 |
| 2013/0171599 A1 | * | 7/2013 | Bleich | A61B 5/0456 434/247 |
| 2014/0277241 A1 | * | 9/2014 | Bleich | A61N 1/36585 607/18 |
| 2015/0297109 A1 | * | 10/2015 | Garten | A61B 5/04845 600/544 |

FOREIGN PATENT DOCUMENTS

CN 104224168 A * 12/2014 ........... A61B 5/7203

* cited by examiner

*Primary Examiner* — Max F Hindenburg
(74) *Attorney, Agent, or Firm* — Staniford Tomita LLP

(57) ABSTRACT

A wearable device has a core contraction sensor. Signals from the core contraction sensor are transmitted to a processor which analyzes the core contraction signals and determines if the user's core is contracted or relaxed. The processor can cause a computing device to output a sequence of tones in response to a core contraction signal. The sequence of tones can correspond to a song which can be played by performing a plurality of core contractions with durations that correspond to a duration of the notes in the song. Alternatively, the core muscles can be contracted to correspond to music heard by the user. The processor can output a score based upon the matching of the core contractions with the musical notes.

18 Claims, 31 Drawing Sheets

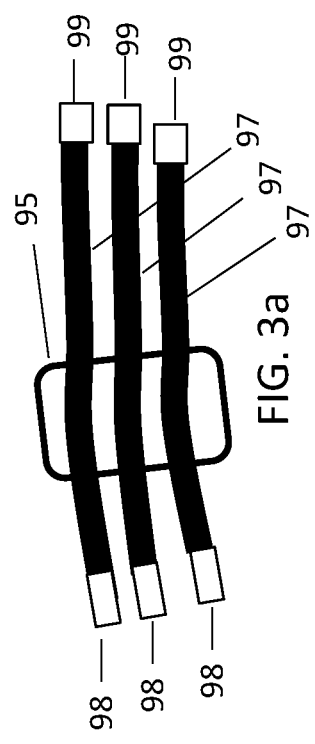
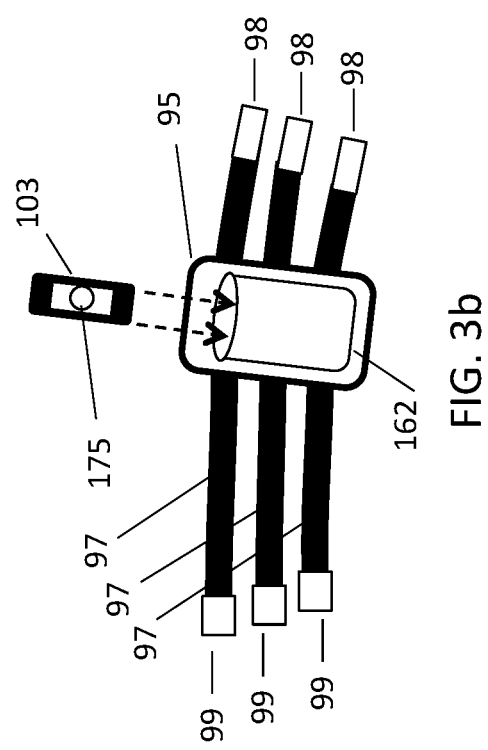

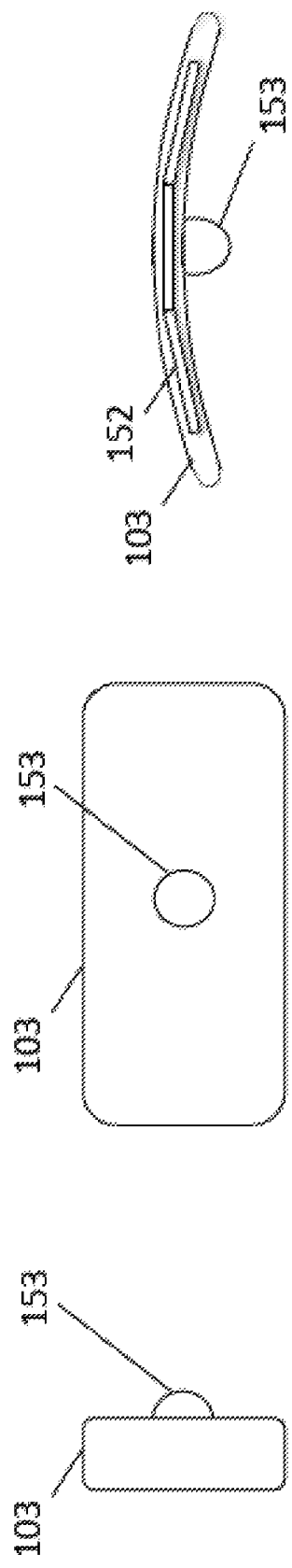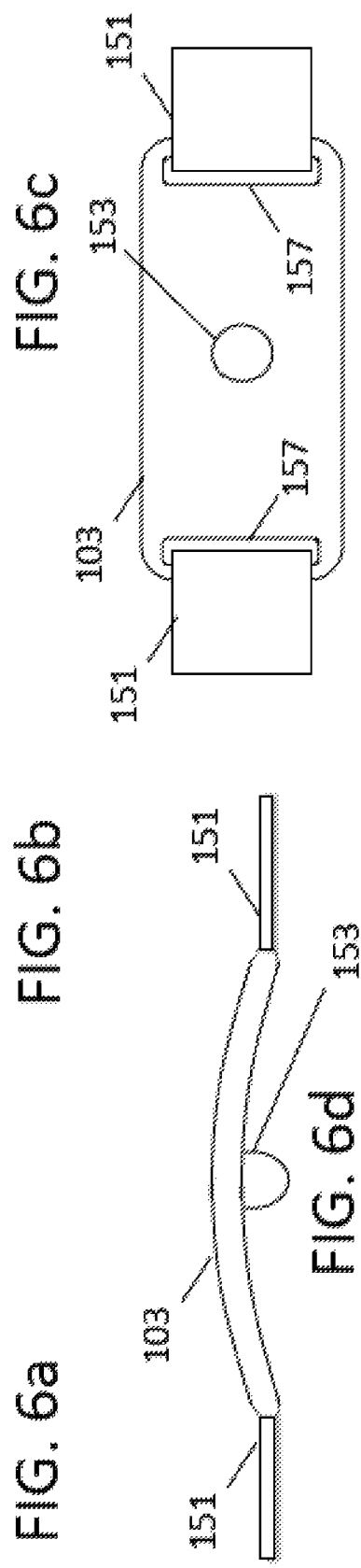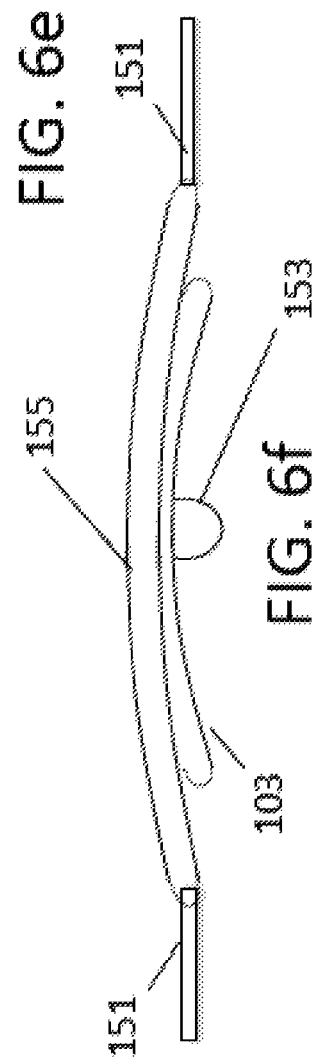

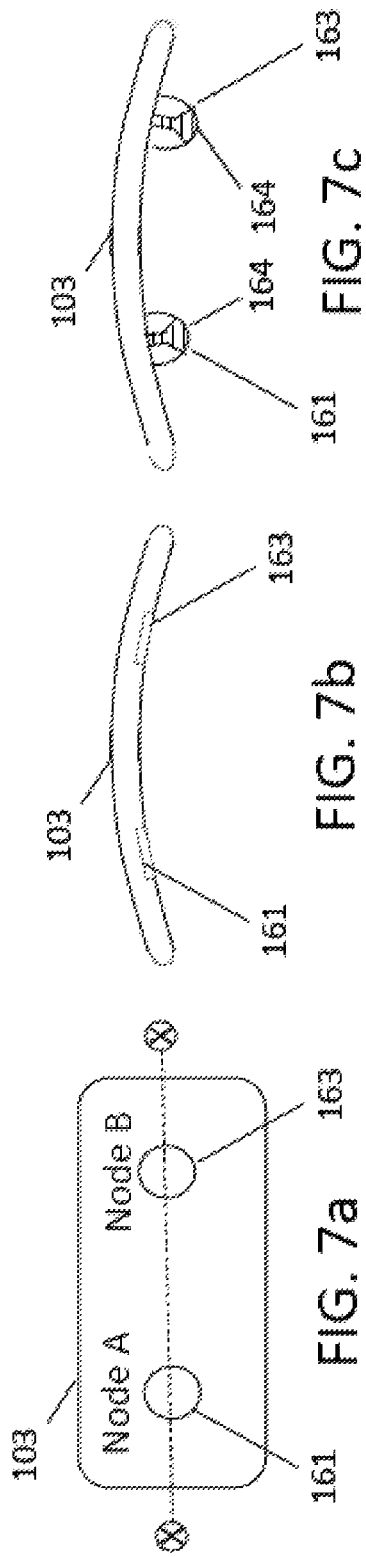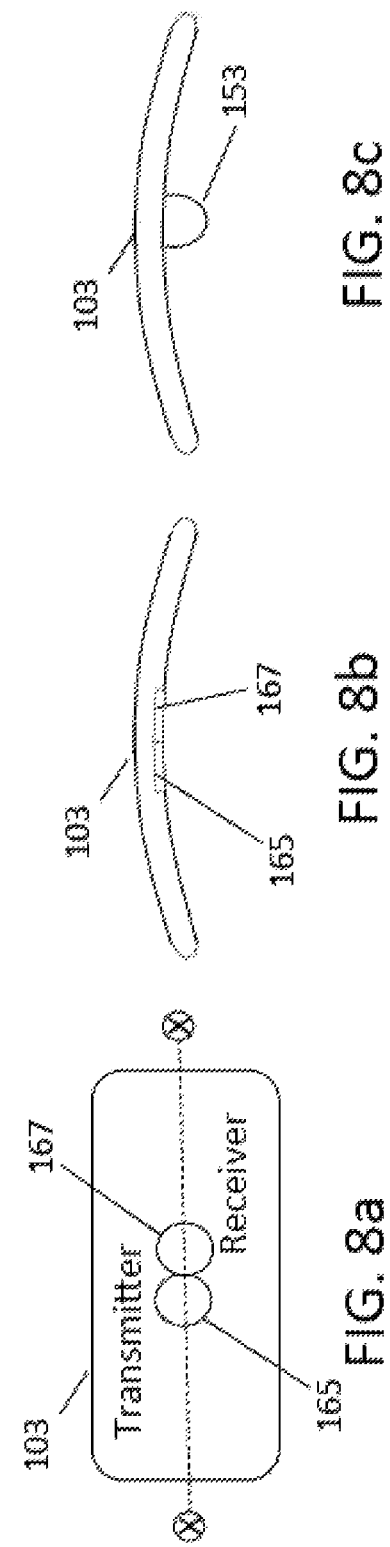

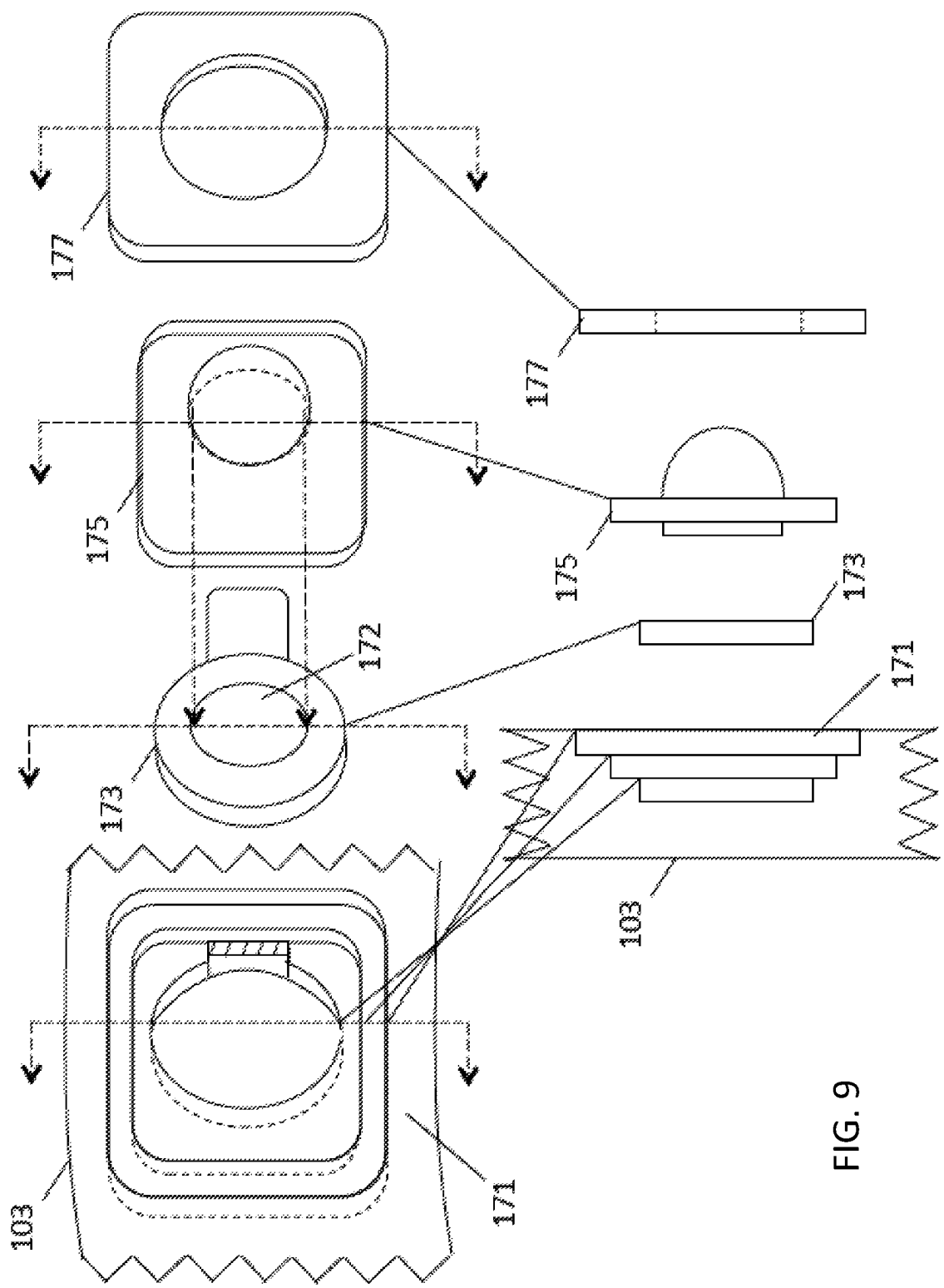

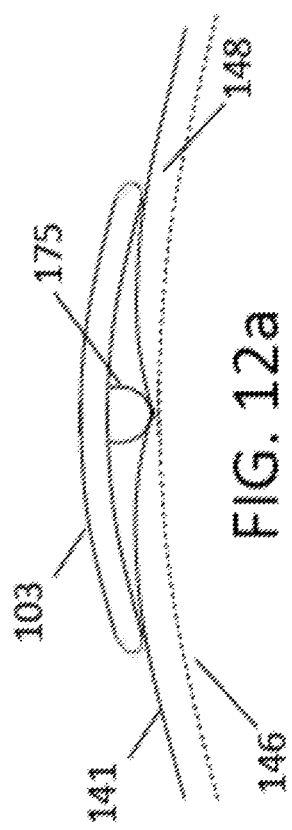
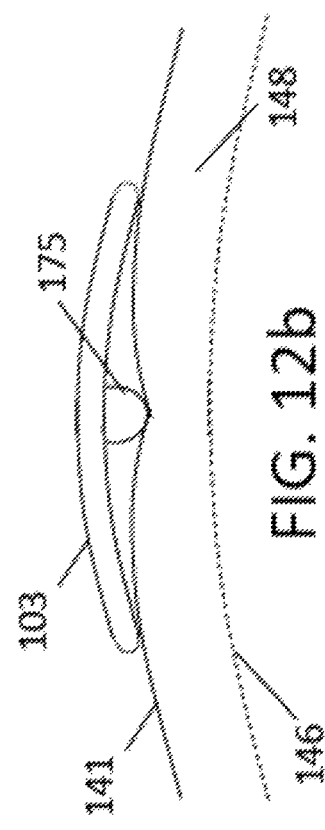
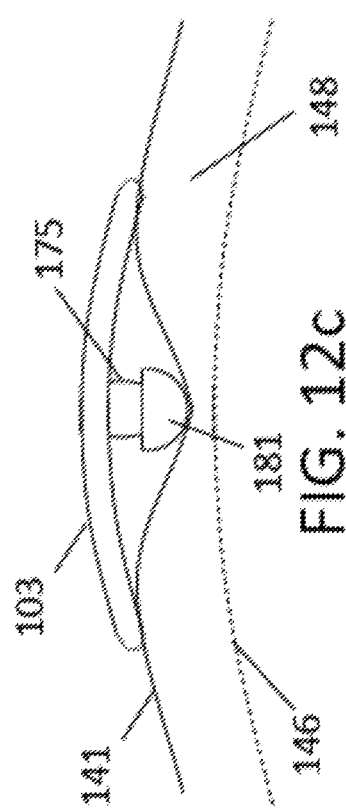
FIG. 12a
FIG. 12b
FIG. 12c

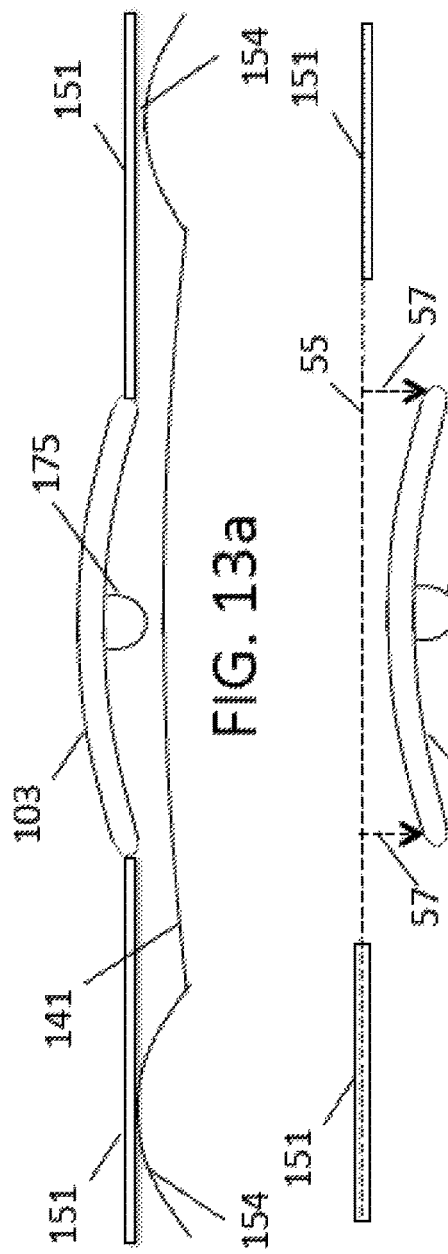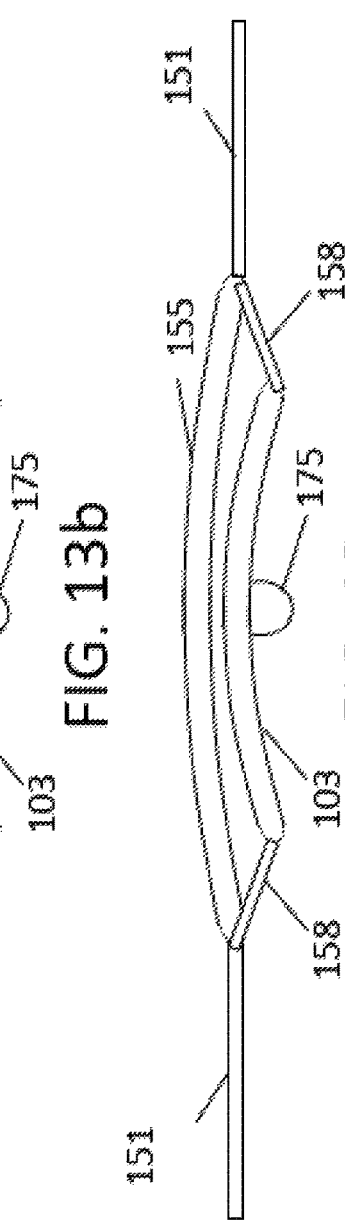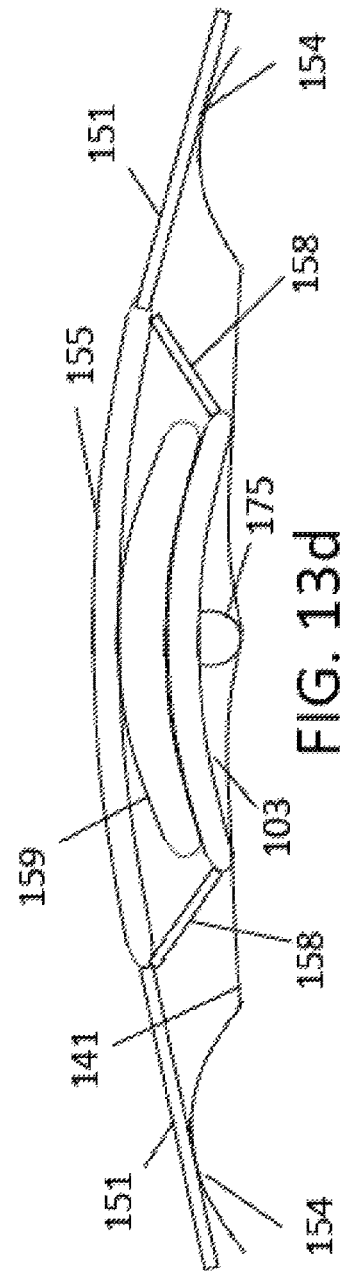

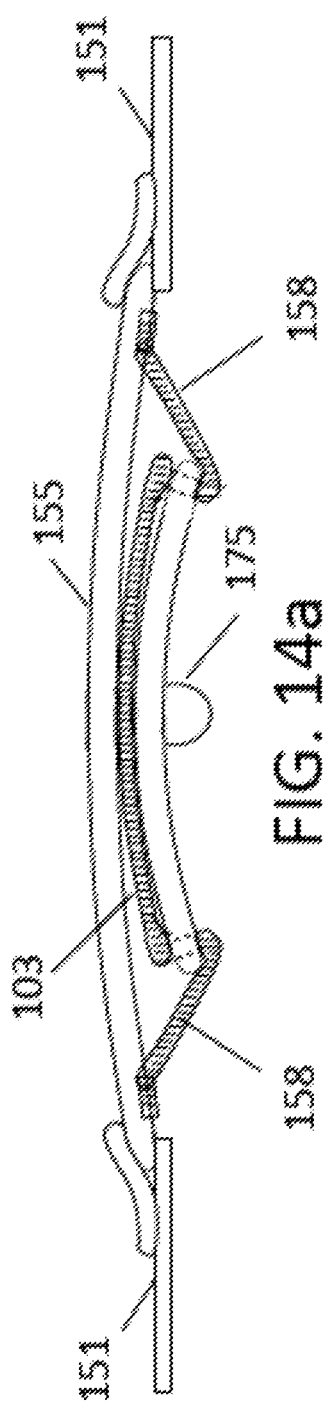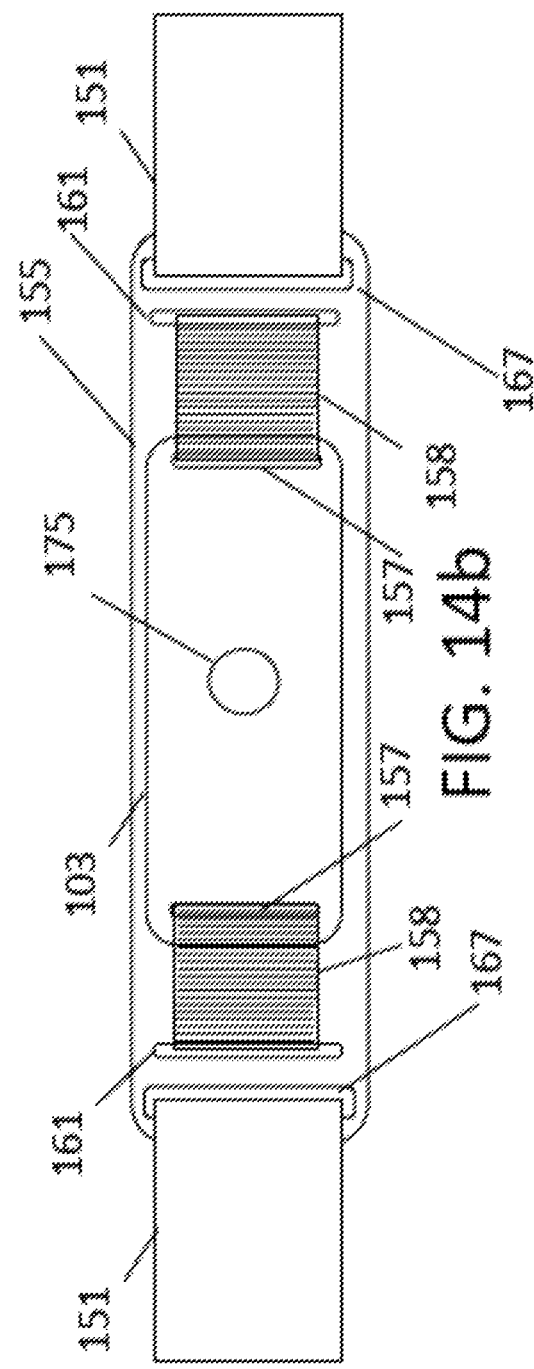

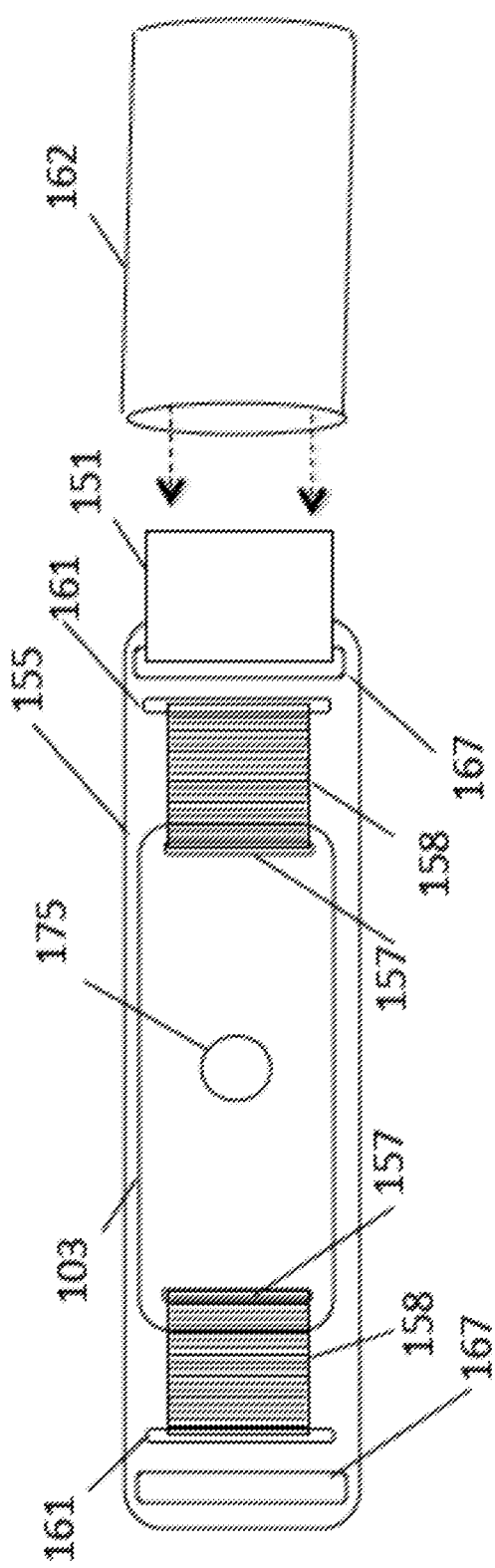
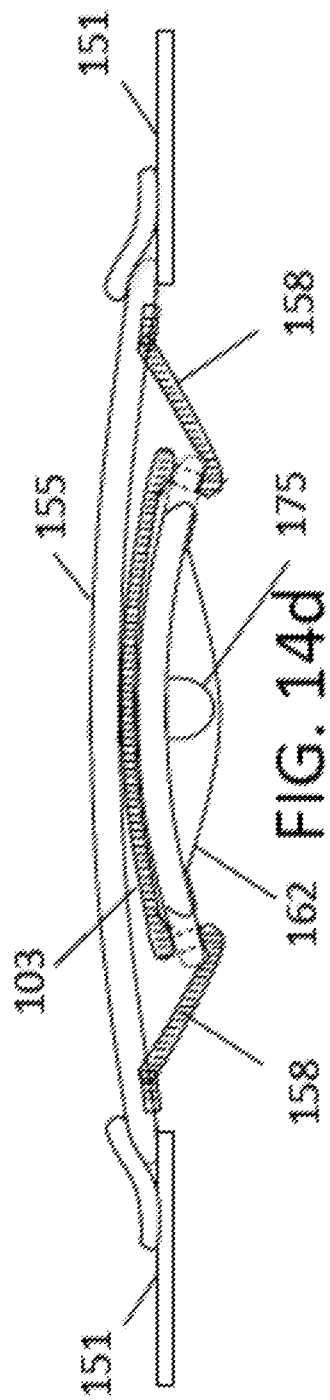
FIG. 14c
FIG. 14d

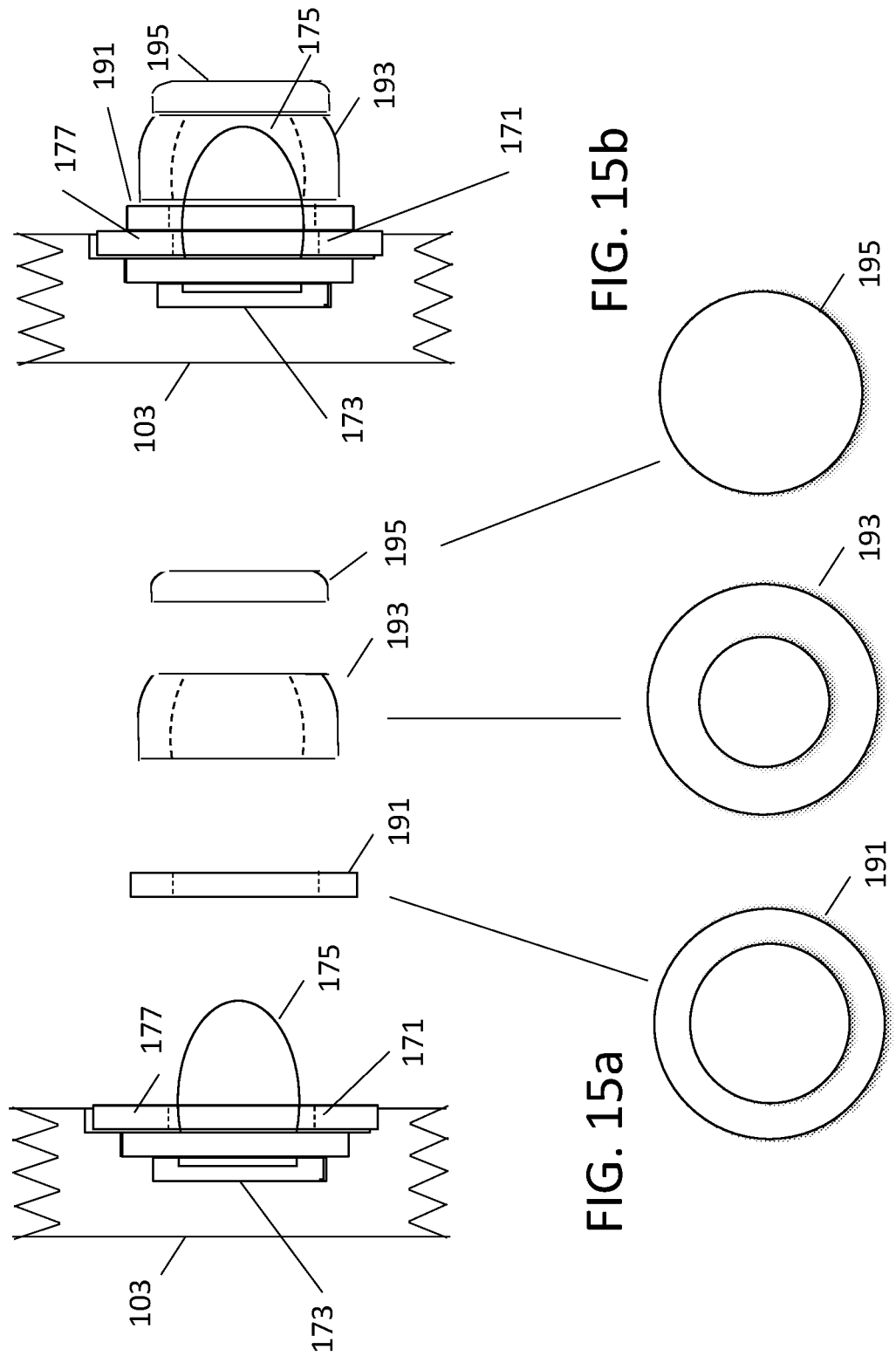

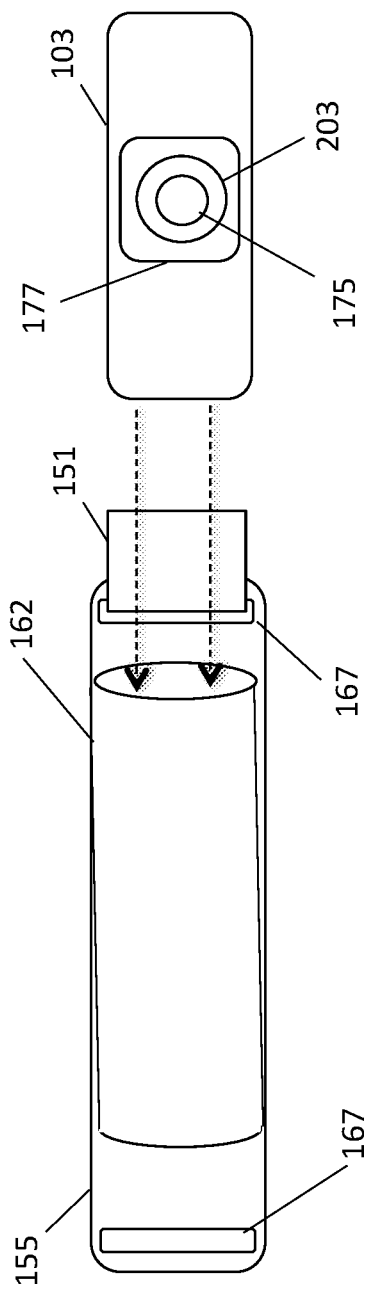
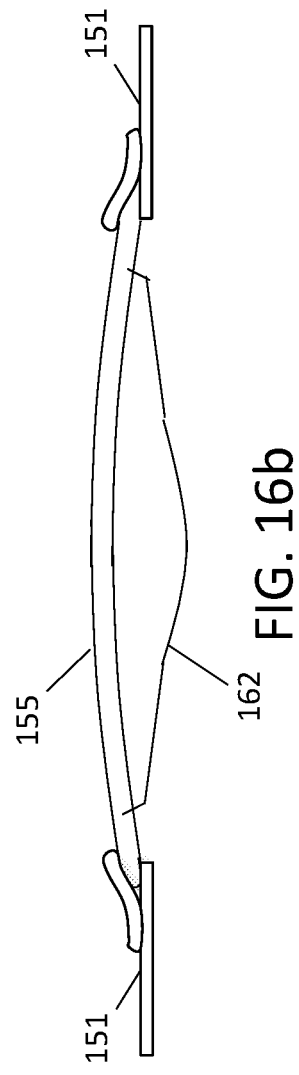
FIG. 16a
FIG. 16b

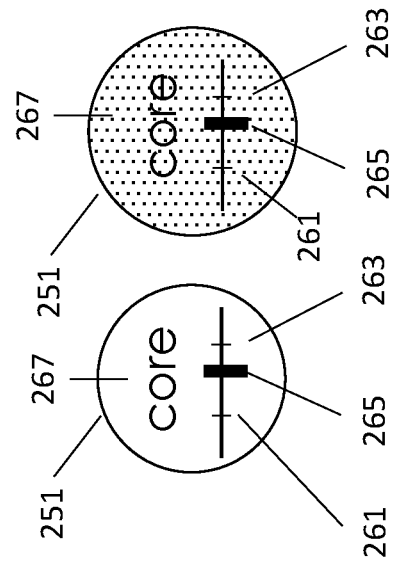
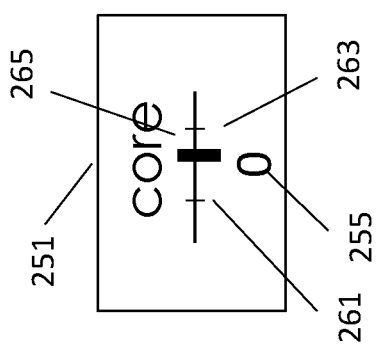
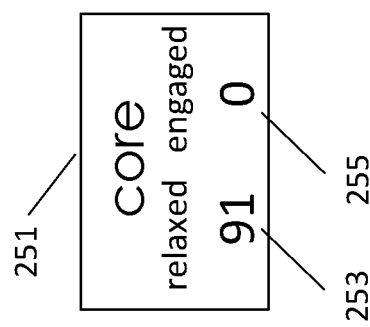
FIG. 21a  FIG. 21b  FIG. 21c  FIG. 21d

SYSTEM AND METHOD FOR DEVELOPING CORE MUSCLE USAGE EMPLOYING MUSIC

CROSS-REFERENCE TO RELATED APPLICATIONS

This application also claims priority to U.S. Provisional Application No. 62/154,626, entitled "System And Method For Developing Core Muscle Usage Employing Music", filed Apr. 29, 2015. This application is also a continuation in part of U.S. patent application Ser. No. 14/789,136, entitled "Apparatus And Method For Teaching And Algorithms For Identifying Qualifying Movements", filed Jul. 1, 2015, which is a continuation in part of U.S. patent application Ser. No. 14/132,808, entitled "System, Apparatus, And Method For Promoting Usage Of Core Muscles And Other Applications", filed Dec. 18, 2013, now U.S. Pat. No. 9,226,706 which claims priority to U.S. Provisional Application No. 61/739,160, entitled "System For Promoting Usage Of Core Muscles And Other Applications", filed Dec. 19, 2012. The disclosures of U.S. Pat. No. 9,226,706 and U.S. patent application Ser. Nos. 14/652,542, 14/789,136, 14/817,964, 62/154,626, 62/166,093 and 62/189,812 are hereby incorporated herein by reference in their entireties.

FIELD OF THE INVENTION

Embodiments disclosed relate to systems and methods for development of core muscles by using music in conjunction with detecting core muscle usage. Embodiments also relate to apparatus, systems and methods for discriminating between multiple identified movements, recognizing core muscle activity or lack of it thereof in those identified movements, and providing feedback to the user regarding a correct or incorrect core muscle use, acknowledging a core muscle contraction when appropriate, informing of an inappropriate core muscle contraction, and identifying a movement wherein a core muscle contraction is not performed but could be performed.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

In recent years, there has been explosive growth in the number of portable and handheld devices that include but are not limited to sensors such as accelerometers, gyros, magnetometers, altimeters, and/or pressure sensors. Examples of such devices include smart phones, cell phones, gaming devices, and wearable devices (or wearables).

In gaming devices, tilt or angles of rotation are often tracked and used to control elements of the game. A large number of wearables target health and fitness applications where steps taken and flights of stairs taken by device users are tracked utilizing accelerometers and altimeters.

Inertial navigation is a method utilizing accelerometers, gyroscopes or gyros, and a microprocessor contained on a moving object to continuously calculate device positions utilizing dead reckoning the position, orientation, and velocity of the object. Dead reckoning is the process of calculating the current position by using a previously determined position and advancing that position based on estimated speeds over known elapsed time. A system implementing inertial navigation is self-contained and requires no external references. Inertial navigation has generally been used by aircraft, spacecraft, guided missiles, and ocean craft. Inertial navigation may be used in embodiments of the inventive concepts described in this disclosure targeting systems and devices for the wearables market.

Most health and fitness wearables on the market today may track one or more of the following: steps taken, number of stairs taken, heart rate, movement activity, and sleep patterns. These devices generally utilize accelerometers, altimeters, light sources and sensors, and voltage sensors to sense and detect the parameters they measure and track.

Back injuries are a common problem. Core muscle based support can be used as a means for improving back support and preventing back injuries. What is needed is a system and method for improving core based support through core muscle contraction exercise and usage training.

SUMMARY OF THE INVENTION

In U.S. patent application Ser. No. 14/132,808, entitled "System, Apparatus, And Method For Promoting Usage Of Core Muscles And Other Applications", filed Dec. 19, 2013, an inventive system is presented including a wearable device which monitors a user's movements for Qualifying Movements (QM), where a QM is a movement for which support from contraction of the core muscles may be beneficial to the lumbosacral junction and lumbar spine. When a QM is identified, the system determines whether or not the QM is protected or not protected based on the status of the user's core before, during, and after the QM. Objectives of the system include: having the user contract their core muscles during the time the stress on the lumbar spine and lumbosacral junction is greatest during a QM; and having the user develop the habit of contracting their core muscles during QMs such that they continue this beneficial practice even without the system. In general, if the core is contracted before and during the QM, the QM may be considered protected. However, since it is protecting the lumbosacral junction and lumbar spine when the stress is greatest that matters most, having the core contracted during periods when, for example, the acceleration or deceleration is greater than a threshold may also result in a QM being considered protected. An overall objective of the system is to provide system and method for developing core muscle usage employing music.

The wearable device and application software (app) described in this patent application and U.S. patent application Ser. No. 14/132,808 have been described as devices to develop usage of the core muscles. The wearable and app may also be used to monitor other muscles and other body movements. For example, after a knee surgery, the Vastus Medialis Oblique (VMO) muscle will tend to atrophy. The inventive apparatus and system may be used in a modified strap that is placed over the VMO. As the user changes from the seated position to the standing position, it may be desirable that the user engages the VMO prior to and through the seated to standing movement. The monitoring of the movement of the thigh and contraction of the VMO may be monitored in a manner similar to the monitoring of the core muscle contractions during a qualifying movement. This modified VMO system can also provide feedback to the user in a similar manner.

The present description will focus mainly on development of the core muscles. However, the inventive concepts described here and in the other descriptions may be applied to the development and training of other muscles. The VMO is one example. In other embodiments, the inventive system can be used to monitor other muscle contractions with a muscle contraction sensor secured around or to the muscle being monitored.

A tone is the simplest sound distinguishing one note from another and containing only one frequency. In contrast, a note can be a tone played from an instrument. However; the note played by the instrument can include the tone, but will also have harmonics, which distinguish one instrument from another. Also, a note may be limited to one of 12 notes in a plurality of chromatic scales. Some music nay not be limited to 12 notes in a scale and some of the scales use different frequency relationships between the notes.

In an embodiment, the system disclosed in this application compares the timing of musical tones heard by a user with core contractions detected by a core contraction sensor. A user can hear a song, which provides a specific sequence of musical tones or notes. The user interface can instruct the user to contract the core muscles when each of the musical tones or notes are heard and release the core muscles when the musical tones or notes stop or change. A core contraction sensor in communication with a processor can be used to detect the core contractions of the user. The core contraction sensor can be a wearable device, which can emit core contraction signals to the processor. In an embodiment, the core contraction sensor can be coupled to a wireless transmitter which can be received by a wireless receiver coupled to the processor. If the core contractions correspond with the musical notes, the system can inform the user that the core contraction was performed correctly. Conversely, if the system detects that the core contraction was not performed or under performed the user interface can inform the user of the core contraction errors.

In an embodiment, the processor can receive core contraction signals from the core contraction sensor and the processor can be coupled to a memory and a speaker or other audio output device. Music can be stored in the memory and any stored musical song can be selected by the user through a user interface. The processor can play the music and the user can respond to hearing the music by contracting the core muscles. In another embodiment, the processor can be coupled to a microphone which can detect ambient musical notes. The processor can detect the musical notes as they are received and compare the detection of the notes to the detection of the core contraction.

Since the user will typically be responding to the musical notes, the core contraction reactions will occur shortly after the musical notes are detected. The processor can determine if the core contractions correspond to the musical notes played or detected by the system. The processor can respond to the detected core contractions by outputting feedback information to inform the user if the core contractions have been performed correctly. The processor can provide positive feedback when a core contraction corresponds to a musical note and negative feedback when the core contraction is not detected or does not correspond to a musical note. This feedback can be in the form of a cumulative core score for a plurality of core contractions and musical notes. For example, the system can provide a feedback score for each song processed by the system.

In yet another embodiment, a user can contract the core muscles and the core contraction can be detected by the core sensors. The core contraction signals can be transmitted to a processor which can respond to the core contraction signals by emitting a first tone from a sound generator to a speaker. The tone can be emitted for a predetermined fixed length of time or for as long as the user's core muscles are contracted and the core contraction sensor is actuated. Once the user releases the core muscles, the core contraction sensor will cease to transmit the core contraction signal and the processor will discontinue the tone output from the speaker. The user can contract the core muscles again and in response to the core contraction signal the processor can cause the device to emit a second tone from the sound generator to the speaker. These tones can be notes from a sequence of notes from a song stored in memory. If the user knows the song, the durations of the notes can correspond to the user's memory of the song. By controlling the muscle contractions, the song can be played accurately. In an embodiment, a visual interface may be provided in which causes symbols or words to scroll across a display to allow a user to anticipate notes and when to contract his or her core muscles. In an embodiment, music accompaniment may be provided.

In another embodiment, the tones or notes may be selected from an instrument selection button on a graphical user interface (GUI) on the app display. For example, a user may select a piano from the GUI resulting in the image of a piano keyboard being shown on the display. In most applications, a limited number of keys may be shown. In some applications, fewer than two octaves of keyboard keys may be shown. In other applications two or more octaves of keyboard keys may be shown. The user may select a note by touching a key on the keyboard shown on the GUI. A user can engage the core muscles and the core contraction can be detected by the core sensors. The core contraction signals can be transmitted to a processor which can respond to the core engagement signals by emitting the selected note from a sound generator to a speaker. The duration of the note may be fixed or related to the time duration that the core muscles are identified as being engaged (contracted) by the processor. Once the user relaxes the core muscles, the core contraction sensor will cease to transmit the core contraction signal and the processor will identify the relaxed condition of the core muscles. The user can touch a second note on the keyboard GUI and contract the core muscles again and in response to the core contraction signal, the processor can cause the device to emit a second note from the sound generator to the speaker. The described process may continue, enabling the user to perform a song. In an embodiment, a visual interface may be provided in which symbols or words scroll across a display to allow a user to anticipate notes and use the visual information to determine when to contract his or her core muscles. In an embodiment, music accompaniment audio output from a computing device may be provided.

In another embodiment, instead of tones that are notes from a sequence of notes from a song stored in memory, words from a sequence of words which can be from a document, pledge, or creed may be stored in memory. A user can engage the core muscles and the core contraction can be detected by the core sensors. The core contraction signals can be transmitted to a processor which can respond to the core engagement signals by emitting a first word from a sound generator to a speaker. Once the user relaxes the core muscles, the core contraction sensor will cease to transmit the core contraction signal and the processor will identify the relaxed condition of the core muscles. The user can contract the core muscles again and in response to the core contraction signal, the processor can cause the device to emit a second word from the sound generator to the speaker. The described process may continue until each of the words in the sequence of words stored in electronic memory is completed. As discussed, the stored words may be from a document, pledge, or creed. In an embodiment, portions of words such as some syllables of each word or sequences of words may be emitted from an audio output for each core engagement.

In other embodiments, music, voice, or any recording including audio or video may be stored in memory and output for synchronized core contraction through an audio output. A user can engage the core muscles and the core contraction can be detected by the core contraction sensors. The core contraction signals can be transmitted from the contraction sensors to a processor which can respond to the core engagement signals by emitting a first portion of the audio recording on a playback device through an audio output device. The audio output playback device may include a speaker and display when appropriate. Once the user relaxes the core muscles, the core contraction sensor will cease to transmit the core contraction signal and the processor will identify the relaxed condition of the core muscles. When the relaxed condition of the core is identified, the playback from the audio output may stop. The user can contract the core muscles again and in response to the core contraction signal, the processor can cause the device to emit a second portion of the recording on a playback device. The process may continue until playback of the entire recording is complete. In an embodiment, a visual interface in communication with the processor may be provided in which symbols or words scroll across a display to allow a user to anticipate when to contract their core muscles. Signal processing techniques may be applied to the signals prior to playback to ensure a comfortable experience for the user. Signals may be filter for a smooth turn on transient and a smooth turn off transient.

In different embodiments, the inventive system can be a run on a mobile computing device, which can be a smart phone, a tablet, a smart watch, or a dedicated computing device. If mobility is not required, the system can run on any computer. The computer program used to perform the described processes can be downloaded from a server and stored in memory coupled to the processor of the mobile computing device. The user can select the computer program through a touch screen user interface. For music that is stored and accessed by the processor, information about the musical notes can be displayed on a screen of the computing device so that the user will have both visual and audio in order to receive the core contraction signals.

The core contraction is useful in performing protected qualifying movements which are qualifying movements that are performed with the core muscles properly contracted during the qualifying movements. The protected qualifying movements and contraction sensor wearable devices are described in more detail in U.S. Pat. No. 9,226,706.

A comprehensive method to teach users to contract their core to protect QMs is also needed. Connecting this musical teaching method with a device and system to provide immediate and continuous feedback during training and practice sessions with effective core contraction identification would be beneficial to users, as well as therapists, trainers, and others teaching regular contraction of the core to clients and patients.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIG. 3a illustrates a back view of an embodiment of a wearable device holder.

FIG. 3b illustrates a front view of an embodiment of a wearable device and wearable device holder.

FIG. 6a illustrates a side view of an embodiment of the wearable device and core sensor interface.

FIG. 6b illustrates a front view of an embodiment of the wearable device and core sensor interface.

FIG. 6c illustrates a top view of an embodiment of the wearable device and core sensor interface showing an internal compartment to house electronics, sensors, and a battery.

FIG. 6d illustrates a top view of an embodiment of the wearable device and core sensor interface attached to a belt.

FIG. 6e illustrates a front view of an embodiment of the wearable device and core sensor interface attached to a belt.

FIG. 6f illustrates a top view of an embodiment of the wearable device and core sensor interface attached to a strap with the strap attached to a belt.

FIG. 7a illustrates a front view of an embodiment of the wearable device and core sensor interfaces utilizing two nodes for core contraction sensing.

FIG. 7b illustrates a top view of an embodiment of the wearable device and core sensor interfaces utilizing two non-protruding sensing nodes.

FIG. 7c illustrates a top view of an embodiment of the wearable device and core sensor interfaces utilizing two protruding sensing nodes.

FIG. 8a illustrates a front view of an embodiment of the wearable device and core sensor interfaces for core contraction sensing having a transmitter and a receiver.

FIG. 8b illustrates a top view of an embodiment of the wearable device and core sensor interfaces for core contraction sensing using non-protruding sensor interface structures having a transmitter and a receiver.

FIG. 8c illustrates a top view of an embodiment of the wearable device and core sensor interface for core contraction sensing using a combined protruding sensor interface structure having a transmitter and a receiver.

FIG. 9 illustrates an exploded view and a cross-sectional view of an embodiment of a core contraction sensor assembly.

FIG. 12a illustrates a cross sectional view of an embodiment of the device and bumper placed on the core section showing the user's skin and underlying core muscles for a user with less body fat.

FIG. 12b illustrates a cross sectional view of an embodiment of the device and bumper placed on the core section showing the user's skin and underlying core muscles for a user with more body fat.

FIG. 12c illustrates a cross sectional view of an embodiment of the device and bumper with an extender cap placed on the core section showing the user's skin and underlying core muscles for a user with more body fat.

FIG. 13a illustrates a cross sectional view of an embodiment of the device, bumper, and belt on a user with prominent hip bones.

FIG. 13b illustrates a cross sectional view of an embodiment of the device separating from the adjoining line and toward the core muscles.

FIG. 13c illustrates a cross sectional view of an embodiment of the device with a strap connecting both ends of a belt and gap extenders connecting to the device to enable the device to separate from the adjoining line toward the core.

FIG. 13d illustrates a cross sectional view of an embodiment of the device with a gap filler for holding the device against the core on a user with prominent hip bones.

FIG. 14a illustrates a top view of a cross section of an embodiment of the device, bumper, strap, gap extender, and belt.

FIG. 14b illustrates a front view of an embodiment of the device, bumper, strap, gap extender, and belt.

FIG. 14c illustrates a front view of an embodiment of the device, bumper, strap, gap extender, and belt with a tubular shaped material to slide over the device and bumper.

FIG. 14d illustrates a top view of a cross section of an embodiment of the device, bumper, strap, gap extender, and belt with a tubular shaped material positioned over the device and bumper.

FIG. 15a illustrates a cross section of the FSR, bumper, and frame in place with the addition of a flat donut ring and mushroom cap to be placed on the bumper head external to the device.

FIG. 15b illustrates the cross section with the ring and mushroom cap in place.

FIG. 16a illustrates a sock attached directly to the strap allowing the device to be easily slipped into and out of the sock.

FIG. 16b illustrates a top view of the device sitting in the sock, attached to the strap and belt.

FIG. 21a illustrates a button implementation for the app using numbers for the sensorEngaged and sensorRelaxed.

FIG. 21b illustrates a button implementation for the app using a slider for sensorRelaxed.

FIG. 21c and FIG. 21d illustrates a circular button implementation for the app where the radius of the circle changes as the core is engaged.

DETAILED DESCRIPTION

In U.S. patent application Ser. No. 14/132,808, a muscle contraction sensing device and system is described, one embodiment of which enables real-time tracking of the core muscles. The inventive device and system encourage the development of procedural memory for usage of the core muscles. The core contractions can be used during Qualifying Movements (QM) which are defined as movements for which contraction of the core muscles may be beneficial in supporting the lumbosacral junction and lumbar spine.

Figure 1C:
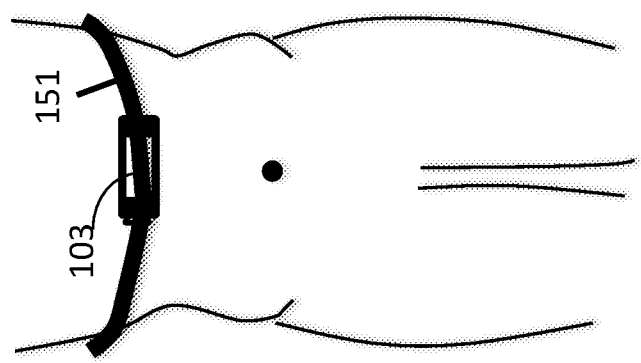
FIGS. 1a, 1b and 1c illustrate a front view of a user wearing an embodiment of the wearable device.
Figure 1B:
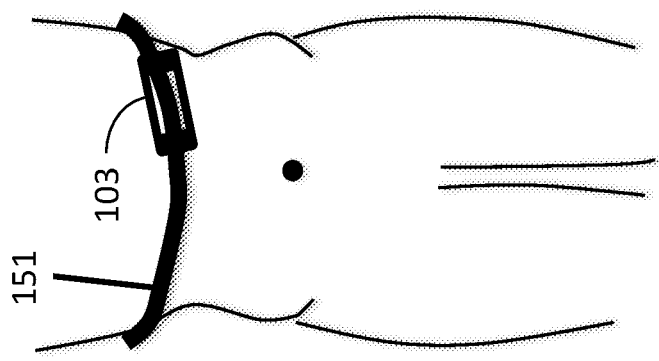
Figure 1A:
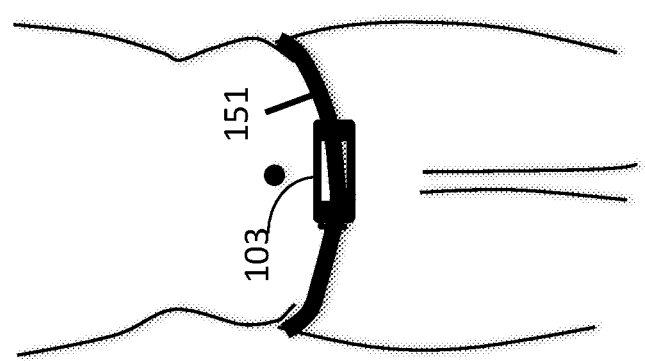
Figure 2B:
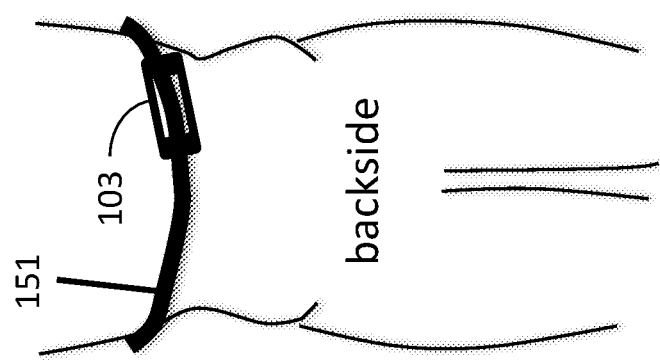
FIG. 2b illustrates a back view of a user wearing an embodiment of the wearable device.
Figure 2A:
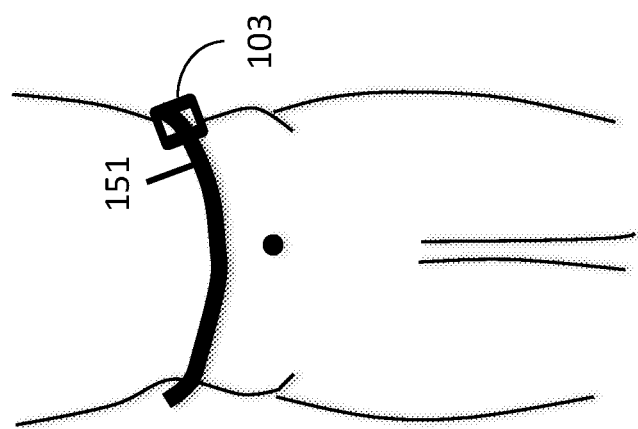
FIG. 2a illustrates a front view of a user wearing an embodiment of the wearable device.

With reference to FIGS. 1a, 1b and 1c, torsos of users are illustrated with core contraction sensors attached to a wearable device 103 with a belt 151 around the torso of the user are illustrated. In FIG. 1a, the wearable device 103 with the core contraction sensor is illustrated below the navel of the user. FIG. 1b illustrates the wearable device 103 with the core contraction sensor below the left ribs of the user and FIG. 1c illustrates wearable device 103 with the core contraction sensor below the solar plexus of the user. FIG. 2a illustrates the wearable device 103 on the side of the user between the ribs and the hip. FIG. 2b illustrates the wearable device 103 on the lower back of the user below the right ribs. The wearable devices described in U.S. Pat. No. 9,226,706 include a core contraction sensor.

Figure 4B:
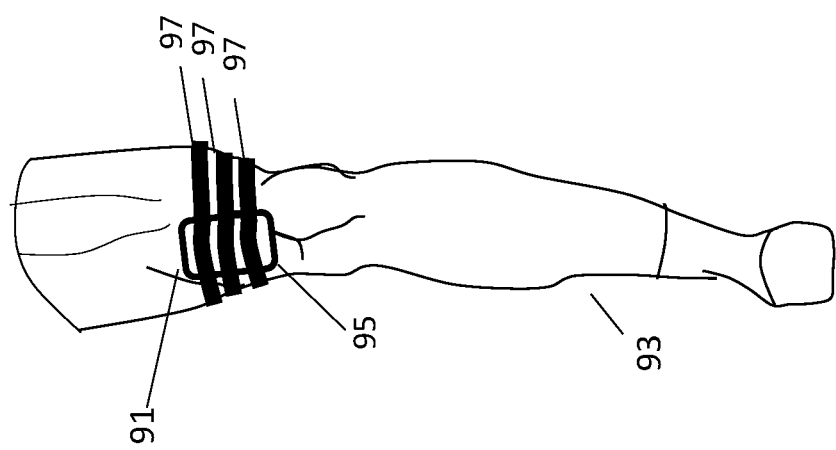
FIG. 4b illustrates a front view of a leg wearing an embodiment of a wearable device.
Figure 4A:
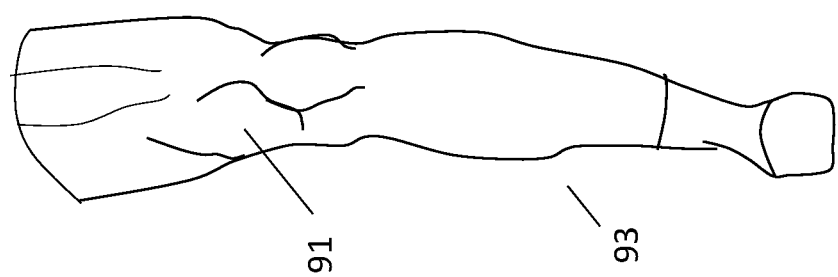
FIG. 4a illustrates a front view of a leg.

An embodiment of the wearable device is shown in FIG. 3a and FIG. 3b, including a strap 95, sock to hold the wearable device 162, belt straps 97, interlocking connectors 98, 99, device 103, and contraction sensor bumper 175. This embodiment may be appropriate to monitor the Vastus Medialis Oblique (VMO) muscle. The VMO is one of the quadriceps muscles in the front thigh. FIG. 3a illustrates the side worn away from the body and FIG. 3b illustrates the side worn against the body. The wearable device and application software described in this patent application and U.S. patent application Ser. No. 14/132,808 have been described as a device to develop usage of the core muscles. The wearable device and app may be used to monitor other muscles and other body movements. For example, after a knee surgery, the VMO muscle may tend to atrophy. The inventive apparatus and system may be used in a modified strap as shown in FIG. 3a and FIG. 3b that is placed around the thigh and that positions device 162 over the VMO to allow muscle contraction sensor bumper 175 to detect changes in firmness of the VMO as it transitions from a relaxed condition to an engaged condition. Referring to FIG. 4*a*, a user's left leg 93 is illustrated from the front view. Toward the inside of the left thigh is the VMO 91. FIG. 4*b* illustrates how the modified strap 95, 97, 98, 99, 162 and wearable device 103 may be placed around the thigh, and how the device 103 may be positioned over the VMO 91.

As the user changes from the seated position to the standing position, it may be desirable that the user engages the VMO prior to and during the seated to standing movement. The monitoring of the movement of the thigh and contraction of the VMO may performed in a manner similar to monitoring movement of the body and contraction of the core during a qualifying movement. For example, when the user is seated, device 103 in position over the VMO may be substantially parallel to the floor under the user. When the user is standing, device 103 may be substantially perpendicular to the floor. Using a movement sensor in the device 103, this change in orientation of the device may be identified similar to the way a qualifying movement is identified. The contraction sensor may be used to identify an engagement of the VMO muscle instead of the core muscles. The processor in the device may process the signals from the movement sensor and the contraction sensor, evaluate relative timing between the signals from the sensors, and provide feedback to the user to aid in physical therapy, rehab, or muscle and movement training.

Figure 5B:
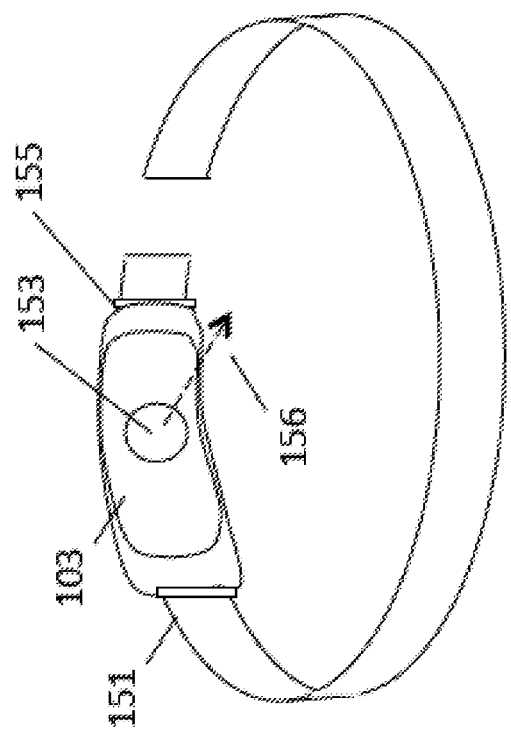
FIG. 5b illustrates an embodiment of a core sensor interface and a wearable device attached to a strap coupled to a belt.
Figure 5A:
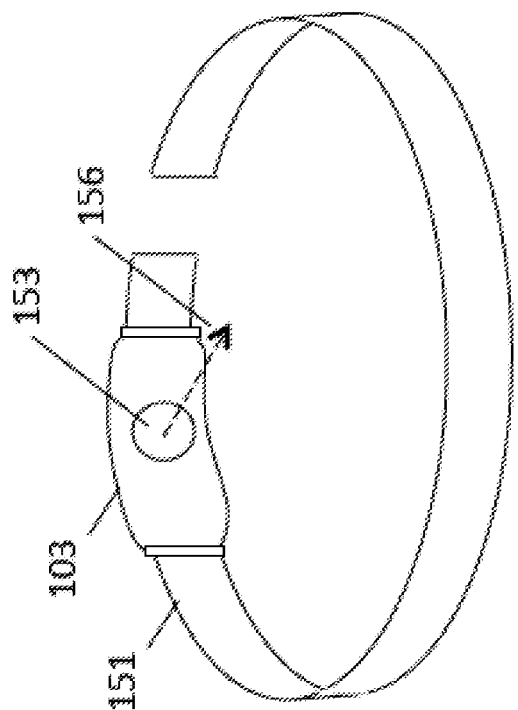
FIG. 5a illustrates an embodiment of a core sensor interface and a wearable device attached to a belt.

An embodiment of the wearable device is shown in FIG. 5*a* including a core sensor interface 153, device 103, and belt 151. This embodiment may be appropriate to monitor the core muscles. The core sensor interface 153 may couple to the user's 101 core muscles in the direction shown by the arrow. The device 103 may include a printed circuit board (PCB) and may contain sensors, a processor, power management electronics, communication electronics, and a battery. The belt 151 may be adjustable in length. In an embodiment, the belt 151 may have at least a portion of a length that is elastic. In another embodiment, the belt 151 may be substantially elastic. In another embodiment, the belt 151 may have no portion that is elastic.

Details of the sensor interface 153 will depend on the specific type or types of sensors used to monitor the core muscles. Some users 101 may have core muscles that are more developed while others may have core muscles that are less developed. Some users may have more body fat over the core muscles while others may have less body fat over the core muscles. In an embodiment, the sensor interface may extrude from the face of the device 103 and may be referred to as a bumper. In an embodiment, the bumper may couple to the core muscles. In an embodiment, the bumper may have a variable height to accommodate variations from user to user in the amount of body fat over the core muscles as well as differing amounts of core muscle development. In an embodiment, the bumper may couple to the user's 101 core muscles in the target core sensing area 145. The inner core muscles generally co-contract, meaning the muscles contract together. While the target core sensing area 145 is an attractive location for attaching the wearable device 103, other locations may be utilized. For example, when the transversus abdominus 135 contracts, the diaphragm 138 may also contract. In an embodiment, the location of the solarplexus below the lungs, between the ribs, and above the abdominal section may be used as the attachment location of the wearable 103.

Another embodiment of a wearable device is shown in FIG. 5*b*. The primary difference compared with the embodiment shown in FIG. 5*a* is the device is attached to an additional element we may refer to as a strap 155. The strap may then connect to the belt 151. The strap may bring benefits to the inventive system that will be described later. Some embodiments of the wearable device 103 may be attached with a belt with a means to control a variable length of the belt 151. Fitting the wearable device may include modifying the adjustable elements to achieve a preferred combination of sensitivity and comfort.

As described in U.S. patent application Ser. No. 14/132, 808, a number of technologies may be used in core sensing to identify a core contraction. For example, a force sensor or pressure sensor may be used. By applying pressure to a device attached against the core muscles, engagement or contraction of the core muscles may result in a pressure change on the device which may be detected by a force sensor or pressure sensor. An embodiment of the device utilizing a force sensor is shown in FIGS. 6*a*-6*f*. In another embodiment, movement sensors may be utilized to detect movements associated contraction of the core muscles. In another embodiment, electromyography or EMG or other sensing techniques utilizing similar principles may be utilized. Electrical current flows into a muscle in order to contract the muscle, and this current may be detected with electrical sensors. The current may be detected by measuring a voltage difference between two points on the skin. In an embodiment of EMG, fine needles may be placed into the muscles being tested. The use of needles directly into the muscles may be more accurate than monitoring the muscles from the surface of the skin. However, needles are quite intrusive for a system that may be used in a variety of settings and by users with little training on how to attach and remove needles. An embodiment of the device utilizing voltage sensing or principles of EMG using sensing on the skin is shown in FIGS. 7*a*-7*c*. In another embodiment, the principles of backscattering may be used. In backscattering, a source signal is transmitted by a transmitter and the reflection of the signal back in the direction from which it was transmitted is measured by a receiver. When the core muscles are contracted, blood flows to the muscles, resulting in changes in the reflected signal. These changes may be identified and associated with core muscle contraction. A number of different types of signals may be used. For example, ultrasound, infrared, and electromagnetic energy may be used. An embodiment of the device backscattering is shown in FIGS. 8*a*-8*c*. In other embodiments, other sensing technologies may be used. Appropriate modifications may be needed to the system to accommodate specific details associated with the implementation of different techniques and technologies.

An example of the system utilizing a force sensor in the form of a force sensing resistor or FSR is shown in FIGS. 6*a*-6*f* and will now be examined in more detail. The side view of the device 103 is shown in FIG. 6*a*, the front view of the device 103 which is the side of the device which will press up against the user's core enabling the core sensor interface 153 to couple to the user's core is shown in FIG. 6*b*. The top view of the device is shown in FIG. 6*c*. The curve shown in FIG. 6*c* may have varying degrees of curvature in different embodiments. In an embodiment, device 103 may have a bendable structure. In an embodiment of the bendable structure, the device may be substantially continuously bendable. In another embodiment, the device may bend in bendable locations. For example, the device may have three sections and bend in the locations between sections. In another embodiment, there may be no curvature. The device may have a cavity 152 to house sensors, electronics, a battery and other components. In FIG. 6*d*, both sides of the device are shown connected to a belt 151. There are number of ways to connect the belt to the device. For example, there may be pass through slits in the device 157 to allow the belt 151 to pass through and connect back to itself as shown in FIG. 6*e*. The belt 151 may connect back to itself using, for example, magnets, clips, snaps, Velcro, or some other fastener. The device 103 may also connect to a strap 155 and the strap 155 may connect to the belt. The strap may be made from a bendable and soft material, or it may be made from a hard material like plastic. Alternatively, it may be made out of a combination of materials. For example, the device 103 may snap into a plastic element that is overmolded by a rubber or other bendable material. Many combinations are possible and may be utilized to meet the requirements of different applications.

Referring to FIGS. 7*a*-7*c*, an embodiment of the device utilizing EMG for the core sensor is shown. Since a potential difference between two nodes may be measured, two conductive ports Node A 161 and Node B 163 may be utilized. A top view of an embodiment shown in FIG. 7*b* shows Node A 161 and Node B 163 as conductive ports embedded in the surface of the device 103. An embodiment shown in FIG. 7*c* shows Node A 161 and Node B 163 as bumpers extruding from the face of the device. In an embodiment, the bumpers are fully conductive. In another embodiment, the bumpers are partially conductive. For example, the bumpers may be conductive at or near the tips of the bumpers and these conductive tips may connect to a conductive section that may connect to electronics within the device. An example of bumpers with conductive tips attached to a conductive center 164 are shown in FIG. 7*c*.

Referring to FIGS. 8*a*-8*c*, an embodiment of the device 103 utilizing backscattering for the core sensor is shown. Backscattering utilizes at least one transmitter 165 and at least one receiver 167. Both are shown as independent ports 165, 167 in FIGS. 8*a*-8*b*. It is shown as a single port 153 in FIG. 8*c*, with both transmitter and receiver combined in a single bumper. The transmitter signal may be audible, for example ultrasound; light, for example infrared; radio frequency or RF; or some other readily creatable signal that may backscatter differently when core muscles are relaxed and contracted. The design of the bumpers may be optimized for the nature of the signals being used.

Referring to FIG. 9, an exploded view of an embodiment utilizing an FSR 173 is shown on the top of the figure while a cross-sectional view is shown at the bottom of the figure. Starting at the upper left and moving to the right, the exploded view includes the device 103 with volume removed 171 to custom fit a force sensing resistor 173 with active area 172, a bumper 175 that may be implemented with a rubber or rubber-like material with a brim, and a frame 177 that holds the force sensing resistor or FSR 173 and bumper 175 in place by holding the brim in place. The frame 177 may be attached to the device using glue or one or more screws or other attachment materials. Additional features may be designed into the brim of the bumper including an O-ring in order to promote water resistance in the design. In the cross-sectional view, the deepest cavity is where the FSR 173 may reside. Above the cavity for the FSR 173 is a cavity where the brim of the bumper 175 may reside. Above the bumper brim is a cavity to fit the frame 177. Note in the cross-sectional view that the bumper 175 may have a small extrusion underneath it to interface to the active portion of the FSR 173. In an embodiment, the feature of the bumper 175 that interfaces to the user's 103 core may be shaped to achieve the objectives of comfort and sensitivity. In the example shown, the section of the bumper that will interface to the user's 101 core is shown to be rounded. In an embodiment, the bumper may have a substantially flat area on the tip that interfaces to the user's 101 core muscles while having a rounded top rim.

Figure 10B:
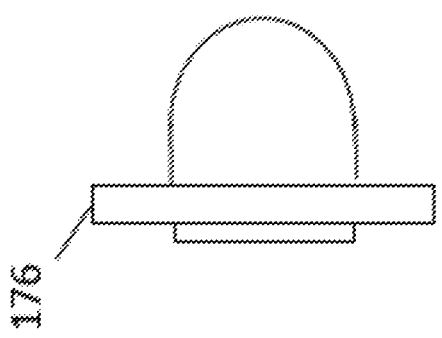
FIG. 10b illustrates an embodiment of a bumper with a second height.
Figure 10A:
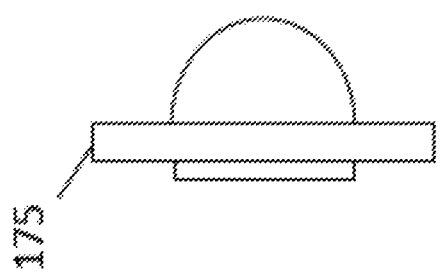
FIG. 10a illustrates an embodiment of a bumper with a first height.

Referring to FIGS. 10*a* and 10*b*, an embodiment may have bumpers with differing height to accommodate the body types of different users. A user with more body fat may benefit from a longer or taller bumper 176 as shown in FIG. 10*b* compared with the shorter bumper 175 shown in FIG. 10*a*.

Figure 11C:
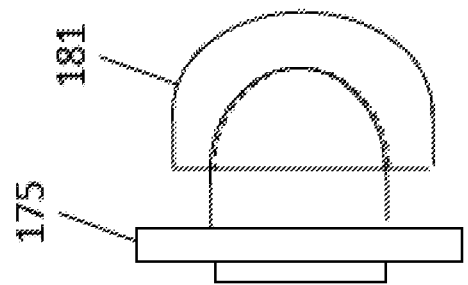
FIG. 11c illustrates an embodiment of a bumper with an extender cap placed on the bumper.
Figure 11B:
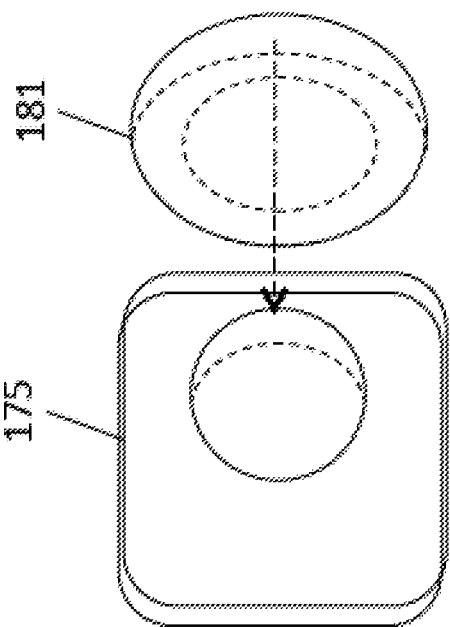
FIG. 11b illustrates a perspective view of an embodiment of a bumper with an extender cap.
Figure 11A:
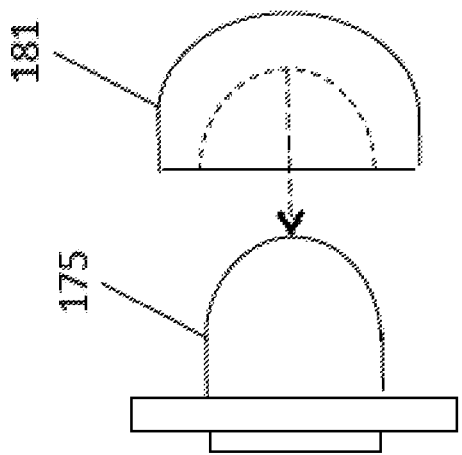
FIG. 11a illustrates an embodiment of a bumper with an extender cap.
Figure 11E:
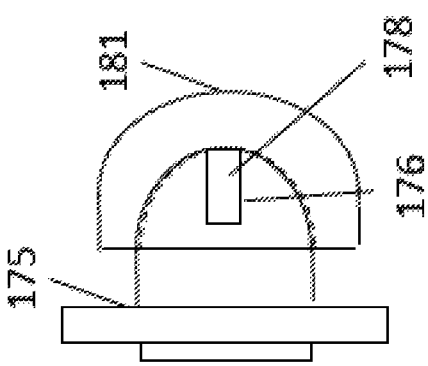
FIG. 11e illustrates an embodiment of the bumper and the extender cap placed on the bumper.
Figure 11D:
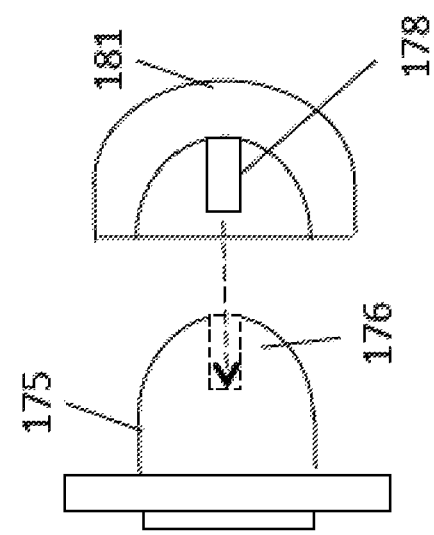
FIG. 11d illustrates an embodiment of a bumper with an additional cavity and an extender cap with an additional extrusion to fit into the additional cavity in the bumper.

Referring to FIG. 11*a*, an embodiment of an extender cap 181 which may be added to the top of the bumper 175 to further extend the effective height of the bumper 175. In FIG. 11*b*, an angled view is shown to further illustrate the extender cap 181 design to extend the effective height of the bumper. A side view of the cap 181 sitting on the bumper 175 is shown in FIG. 11*c*. In an embodiment, different sized caps 181 may be used to provide further variability in order to achieve greater measurement sensitivity while maintaining user 101 comfort. Different techniques may be used to attach a cap to the bumper. For example, the cap 181 may be sized to snuggly fit over the bumper 175 requiring no additional material or elements. Adhesive or double stick tape may be used to connect the cap 181 to the bumper 175. An additional extrusion may be designed into the bottom of the cap 181 to fit into an additional cavity in the bumper 175 as shown in FIG. 11*d* to provide additional stability for the combined structure including the cap 181 and bumper 175 as shown in FIG. 11*e*.

A device 103 with a small sized bumper 175 is shown in FIGS. 12*a* and 12*b*. In FIG. 12*a*, a depiction of a user 103 with less body fat 148 is shown and in FIG. 12*b*, a depiction of a user 103 with more body fat 148 is shown. In FIG. 12*a*, the bumper 175 is near the core muscles whereas the bumper 175 is shown to be far from the core muscles in FIG. 12*b*. In FIG. 12*c*, a taller bumper 175 with a cap 181 is shown with the depiction of the user 103 with more body fat 148. Note that the larger bumper 175 and additional cap 181 enables the sensor interface 153 to reach deeper and nearer to the core muscles.

Referring to FIG. 13*a*, a condition is shown where a user 103 with a small amount of body fat 148 also has prominent hip bones 154. When the belt 151 is used to hold the device 103 near the body, the belt 151 rests on the hip bones 154 which keeps the device 103 a distance away from the core so the bumper 175 is not able to properly contact the target core sensing area 145. Referring to FIG. 13*b*, a conceptual solution is proposed. With belt 151 effectively sitting on the prominent hip bones 154, conceptual adjoining line 55 connects the right and left side belt segments. Conceptually, the inventive solution enables the device 103 to move away from the adjoining line 55 and toward the body as indicated by the arrows 57. Using this approach, the gap between the adjoining line 55 and the target core sensing area 145 may be filled. In FIG. 13*c*, a strap 155 is introduced to continue the adjoining line between the belt segments and the device is attached to the strap 155 via connecting structures referred to as gap extenders 158. Introduction of the strap 155 and gap extenders 158 enables a gap filler 159 to be added between the device 103 and strap 155, which has the effect of pushing the device 103 and subsequently, the bumper 175 toward the user's 101 core muscles as shown in FIG. 13*d*. The gap filler 159 may be made of different types of material, depending on the design choices of the other components. For example, the gap filler 159 may be made of rubber or plastic or an additional appropriate material or materials. The gap filler 159 may be attached using connectors such as clips, Velcro, magnets, snaps, or other attachment techniques such as tongue-in-groove structures.

An embodiment showing all connections of the inventive device packaging is shown from top view in FIG. 14a and shown from the front in FIG. 14b. Slits 167 are cut out of strap 155 to allow the belt 151 to loop through the slits 167 and connect back to itself. It may be sewed to itself, connected by Velcro, or attached by a number of other attachment methods. Slits 167 may be seen in FIG. 14b, while the looping back of the belt to connect to itself is shown in FIG. 14a. The gap extender 158 may be a thin, light, and bendable material which starting from the left side may be attached 161 to the strap 155, pass through slit 157 in the device, pass around between the device 103 and the strap 155, then back through the slit 157 on the right side, and attach on the right side to the strap 155 at location 161 on the right side of the device shown in FIG. 14b. In an embodiment, a very thin material is used for the gap extender 158 to minimize its contribution to thickness between the device 103 and strap 155, and to keep it from keeping the ends of device 103 from contacting the user's 101 core section. In FIG. 14b, the connecting structure 158 is drawn for illustrative purposes thicker than may be desired. In an embodiment, the gap extender 158 may be elastic or partially elastic. In an embodiment, the gap extender 158 may be made of the same or similar material to the strap 155.

In applications where the bumper makes direct contact to a user's 101 skin or to certain materials of clothing, the bumper may stick or grab on to the user's 101 skin or clothing for some angles and amounts of pressure. Referring to FIGS. 14c and 14d, a soft buffer material 162 resistant to sticking or grabbing may be placed over the location where the bumper couples to the user's 101 core muscles. In an embodiment, the stick resistant buffer material 162 may be cotton, polyester, nylon, microfiber or other material, or may be made from a blend of different types of materials. A number of materials are being used and developed for high performance athletic apparel. These materials may be appropriate for stick resistant buffer material. In an embodiment, the stick resistant buffer material 162 may be a type or combinations of types of rubber. In an embodiment, buffer material 162 may be manufactured into the bumper 175 via a surface layer that may be resistant to sticking or grabbing.

Several implementations may be used to hold the buffer material in place. For example, the buffer material 162 may be designed into a tubular shape that slips over the device 103 or portions of or all of the strap 155 which may include the gap extender 158. FIG. 14c shows an example of a tubular shape forming a stick resistant sock 162 to the right of the wearable 103 before it is slipped over the device 103. FIG. 14d shows the stick resistant sock 162 in position over the bumper. In an embodiment, the buffer material 162 may be made from a stretchable material, allowing it to stretch to accommodate different bumper heights. In another embodiment, the buffer material may be made from a material or materials with water resistant qualities. In an embodiment, the stick resistant sock 162 may be made from a material or materials with water resistant qualities, and designed to fit snuggly on both ends over the wearable device 103 as shown in FIG. 14d. The snug fit on the ends of sock 162 may be implemented in a number of ways. An embodiment may utilize a material that stretches. Making the entire sock 162 with stretchable material and designing said sock to fit snugly may result in snug ends when the sock 162 is on the device 103 and the stretchable material may stretch over the bumper to accommodate different bumper heights. Another embodiment may utilize elastic or a material with qualities of elastic that are sewn in or attached to the ends of the sock. Another embodiment may utilize rubber or a material with qualities of soft bendable rubber that may be molded to fit over the device 103, fit snugly on the ends, and have a stretchable area over the bumper or designed with extra volume to accommodate different bumper heights. By combining a design in which all openings to the cavities of the device fit within or under the coverage of the stick resistant sock 162, and making the sock 162 from a material or materials with water resistant qualities with a snug fit on the ends, the combined structure including the device and stick resistant sock 162 may be substantially splash proof from water or other liquids including a user's 101 perspiration. In said design, the strap 155 may have design features to support keeping the sock 162 in position over the device. In an embodiment, the stick resistant sock 162 may be made from a low-cost water resistant material and be designed for a limited number uses and be disposable for certain applications. For example, after using the wearable device with a user 101 during a therapy session, the therapist 107 may remove a limited use and disposable stick resistant sock 162 and put on a new sock 162 for a next user 101.

Figure 14E:
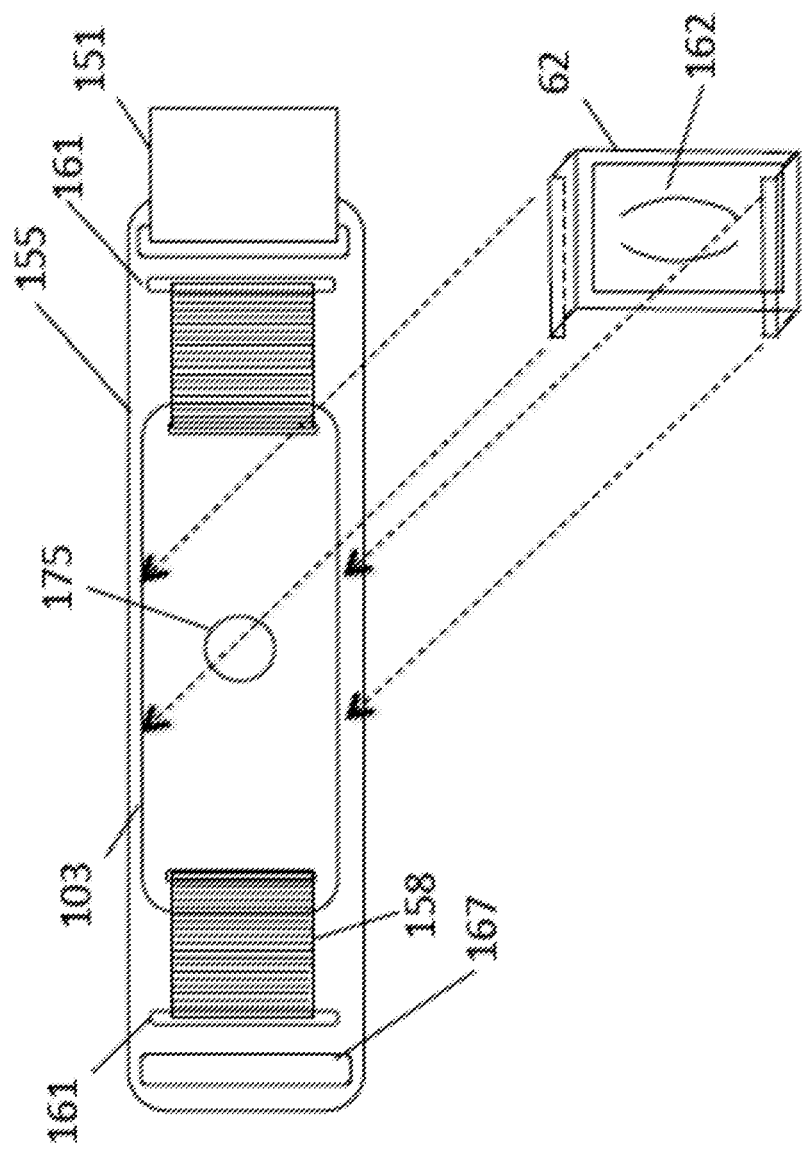
FIG. 14e illustrates an additional element that may snap or clamp onto the face of the device in order to hold material over the bumper.

In other embodiments, the buffer material 162 may be fitted onto an additional element 62 that may snap or clamp on over the face of the device, allowing the bumper 175 to be covered by the buffer material 162 as shown in FIG. 14e. Element 62 may be made out of metal, plastic, or other firm and bendable material. Buffer material 162 may be attached to element 62 using glue, thread (sewed on), or other attachment techniques or materials. In these embodiments, use of water resistant materials for the buffer material 162 and appropriate placement of the element 62 over the device openings may combine to result in a splash resistant wearable device 103. Openings into the device may include an opening to place the PCB, battery, and sensors which may be covered with a fitted cover and held in place by one or more screws, glue, or other attachment devices or materials; ports for battery charging; a communications interface connector which may additionally support battery charging such as USB; and a sensor interface port as described with reference to FIG. 9 which may be covered by a frame and held in place by one or more screws, glue, or other attachment devices or materials.

The inventive sock 162 is an example of a buffer that may be used between the bumper and the user's 101 core. Design elements of the buffer as described may be applied to other implementations to achieve similar objectives. A summary of key design element of the inventive sock 162 may include: a. provides stick or grab resistance between the bumper and the user's 101 skin or clothing; b. with appropriate design of the sock 162 and device 103, the combination may be splash proof; furthermore, the strap 155 and gap extender 158 may be designed to support maintaining the sock 162 in position over the device; c. accommodates different bumper heights or may be designed to fit certain ranges of bumper heights; d. can be made with relatively low material and manufacturing cost and using plastic wrap or thin rubber material may be made disposable; e. may be made from materials used in high performance athletic apparel and may be washed and re-used; and f. simple to remove and replace so may be used by a therapist for multiple users and a new or clean sock 162 may be put on for the start of each user 101 session.

In FIG. 15a, an alternative embodiment to extender cap 181 is shown. The extender cap 181 may increase both height and girth of the bumper. Mushroom cap 193 is similar to extender cap 181 with the feature that the height of the bumper may not be appreciably increased. In an embodiment, the mushroom cap 193 increases the girth but not the height of the bumper. The mushroom cap 193 may result in greater comfort to the user by reducing the sharpness of the bumper. In an embodiment, a flat ring 191 may be placed around the bumper on the face of the wearable device. The ring 191 may keep the mushroom cap 193 from pressing down into the face of the wearable device 103 when pressure is placed on the mushroom cap 193. In an embodiment, the ring 191 may be made from a firm pliable material such as felt, neoprene, or material with similar properties. In some applications, an extender feature may be added to the top of the mushroom cap 191 and bumper 175 in order to increase the height of the contraction sensor. In an embodiment, this feature may be an extender disc 195 as illustrated in the figure. The ring 191, mushroom cap 193, and extender disc 195 can have circular outer circumferences. The ring 191 and mushroom cap 193 can have circular inner diameter center holes. FIG. 15*b* illustrates the ring 191 and mushroom cap 193 placed around and on the bumper 175. Extender disc 195 is shown sitting on top of mushroom cap 193. The mushroom cap 193 may be held in place via a snug fit or with an adhesive such as glue, double stick tape, or other adhesive. Extender disc 195 may be attached using an adhesive such as glue, double stick tape, or other adhesive. In an embodiment, additional features may be designed into the components to facilitate attaching the extender disc 195 or extension feature to the mushroom cap 193.

In FIG. 16*a*, an embodiment with sock 162 attached directly to the strap 155 is shown. Device 103 simply may be slipped into sock 162 with no additional strapping or connecting steps required. Sock 162 may provide splash proof qualities, while providing the buffer role between the device 103 and the user's body or clothing. FIG. 16*b* illustrates a top view of the device 103 sitting in the sock 162 attached to the strap 155. The sock 162 may be attached to the strap 155 by sewing, gluing, Velcro, magnets, or other means of securing or attaching.

Figure 17:
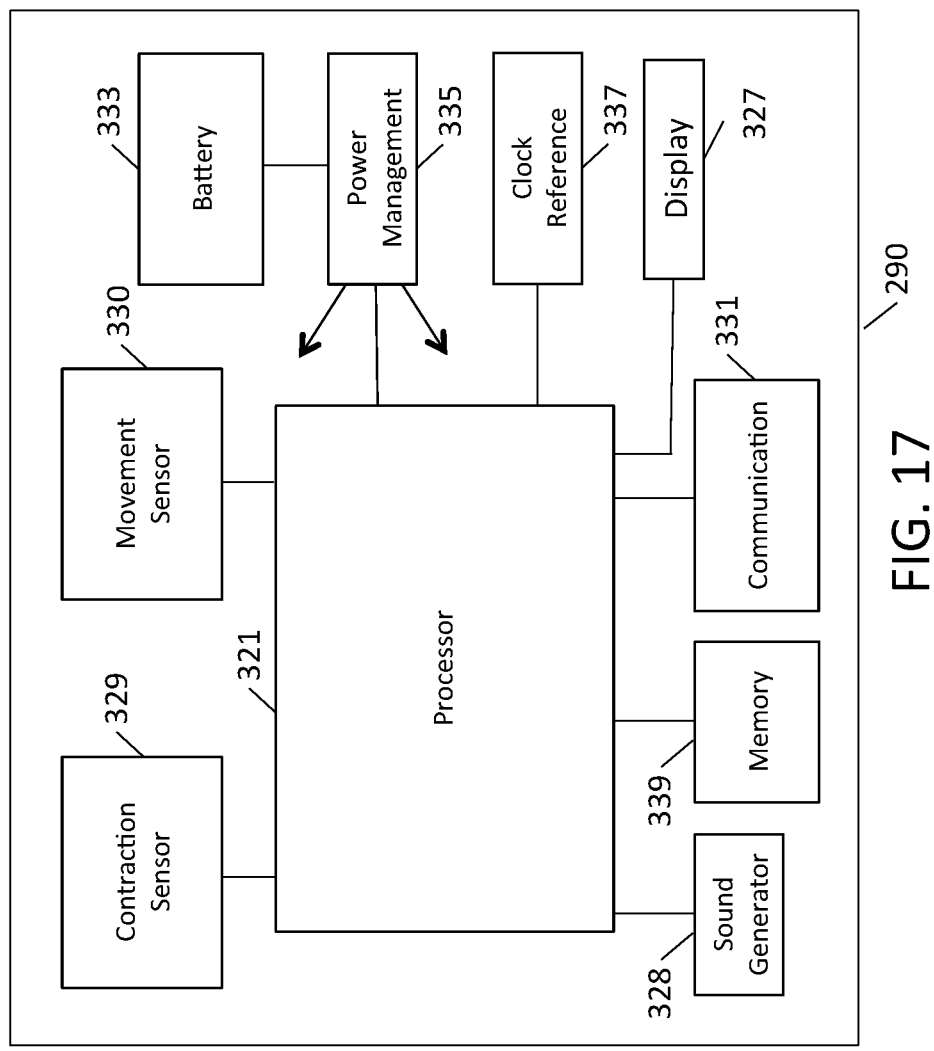
FIG. 17 illustrates a block diagram of the wearable device.

With reference to FIG. 17, a block diagram of an embodiment of the wearable device 290 is illustrated. The processor 321 can also be coupled to various output devices which can provide information to the user which can include one or more of: a sound generator 328 which can emit output signals to the user that indicating correct core contractions during musical tones/notes or incorrect core contractions. In different embodiments, different output devices can be selected. For example, a buzzer or sound generator 328 can be useful at home, but these audio output devices may not be appropriate at an office where other employees will hear the output sounds. An output device such as a light or visual output can be a visual display 327 such as a touch screen which may be useful providing core contraction, music information and feedback to users in areas where others noise can be disruptive to others.

The processor 321 can also be coupled to a communications device 331 that can transmit information to other devices through a wired or wireless communications connection, for example the communications device 331 can be a Bluetooth device that provides wireless communications to other devices. A battery 333 can be coupled to a power management module 335 which can control the distribution of electrical power to the system components. The battery 333 can be rechargeable and capable of being charged with a charger. The processor 321 can also be coupled to a memory 339 which can store musical tone and note information and record user core contraction data. The system can also include a clock reference 337 which can provide a system reference clock to the processor which may also be used to derive sampling clocks for the core contraction sensor 329. If the system has a minimum of intermittent access to date and time information, for example through a cellular system, the clock reference 337 may be utilized in an algorithm using such date and time information so that recorded movements and core contractions can be stored with time stamps.

When a user engages or contracts a muscle, the surface skin region over the muscle being engaged may become firm to the touch and less compressible. When the wearable device is placed on a belt over a muscle that transitions from relaxed to engaged, the change in firmness as the muscle transitions from relaxed to contracted may result in an increase in pressure on the contraction sensor and result in an increase in the contraction sensor value. If a user engages their core muscles employing the technique of hollowing, the contraction sensor value may decrease. Users that utilize the technique of bracing may also have the contraction sensor value decrease when their core is engaged due to body composition and the manner in which they engage their core muscles. In the following, we will assume that when a user engages their core muscles or other muscle being monitored by the wearable device, the contraction sensor value increases. The algorithms may be modified to accommodate the contraction sensor value decreasing when the core muscles or other muscles being monitored are engaged.

The performance of core engagement identification algorithm is critical to the user experience with the wearable device. Let us now investigate some of the important considerations and some inventive embodiments. False positive core engagement identification and missed valid core engagements may be found frustrating to a user and negatively impact the user experience. The inventive approaches described may reduce the frequency that false positives and missed valid core engagements occur.

Figure 18:
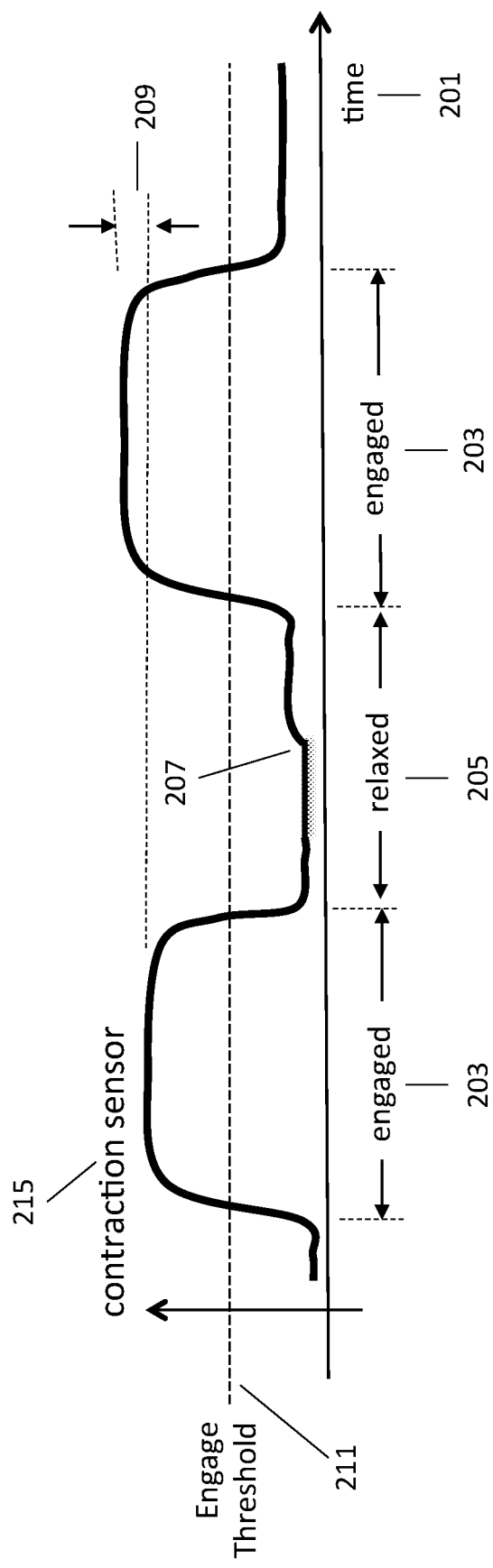
FIG. 18 illustrates features of a signal received from a contraction sensor.

An example of the signal received from the contraction sensor 215 (vertical Y-axis) over time 201 (horizontal X-axis) is shown in FIG. 18. In the example shown, when the user engages the core muscles, the contraction sensor value increases. A sequence of the user's core transitioning from the conditions of engaged 203, to relaxed 205, followed by engaged 203 is shown. In the middle of the relaxed period 205, a small change 207 in the contraction sensor value is shown. This may be the result of the user changing their body position while keeping their core relaxed. This change in body position may change the incident pressure on the contraction sensor which equivalently is the contraction sensor bumper 175. Highlighted in the illustration is the change from the first engaged value to the second 209. This change may result from at least two sources. First, this may be due to a change in core engagement intensity from engagement to engagement. Second, it may be due to different incident pressures of the body on the contraction sensor 175 due to the first engagement being performed in one position, for example sitting, to a second position, for example, standing.

In an embodiment, the Engage Threshold 211 is the level which may define the engaged or relaxed condition. If the contraction sensor value equals or exceeds the Engage Threshold 211, the core may be identified by the algorithm to be engaged. If the contraction sensor value is less than the Engage Threshold 211, the core may be identified by the algorithm to be relaxed. In the illustration of FIG. 18, Engage Threshold 211 is a constant fixed value. The Engage Threshold 211 can be an output signal from the core contraction sensor which can be an electrical resistance value from a FSR. In other embodiments, the Engage Threshold 211 can be any other metric which corresponds to core contraction value such as a digital, force, electrical, pressure, etc. that can be detected or output by the contraction sensor.

Due to the variation in relaxed values due to different body positions and varying belt tightness, the fixed threshold may on the one hand result in false positive core engagement identification, or on the other hand, make difficult getting an engaged core to trigger a core engagement identification. For example, a body movement may result in a larger incident pressure on the contraction sensor moving the relaxed value close to the threshold. As a result, body movements may increase the contraction sensor value above Engage Threshold 211, creating a "false positive" core contraction identification. In another example, with a relaxed core, if a user moves in such a way to decrease pressure on the contraction sensor, then when the user engages their core muscles, the resulting contraction sensor value may be insufficient to exceed Engage Threshold 211.

Figure 19:
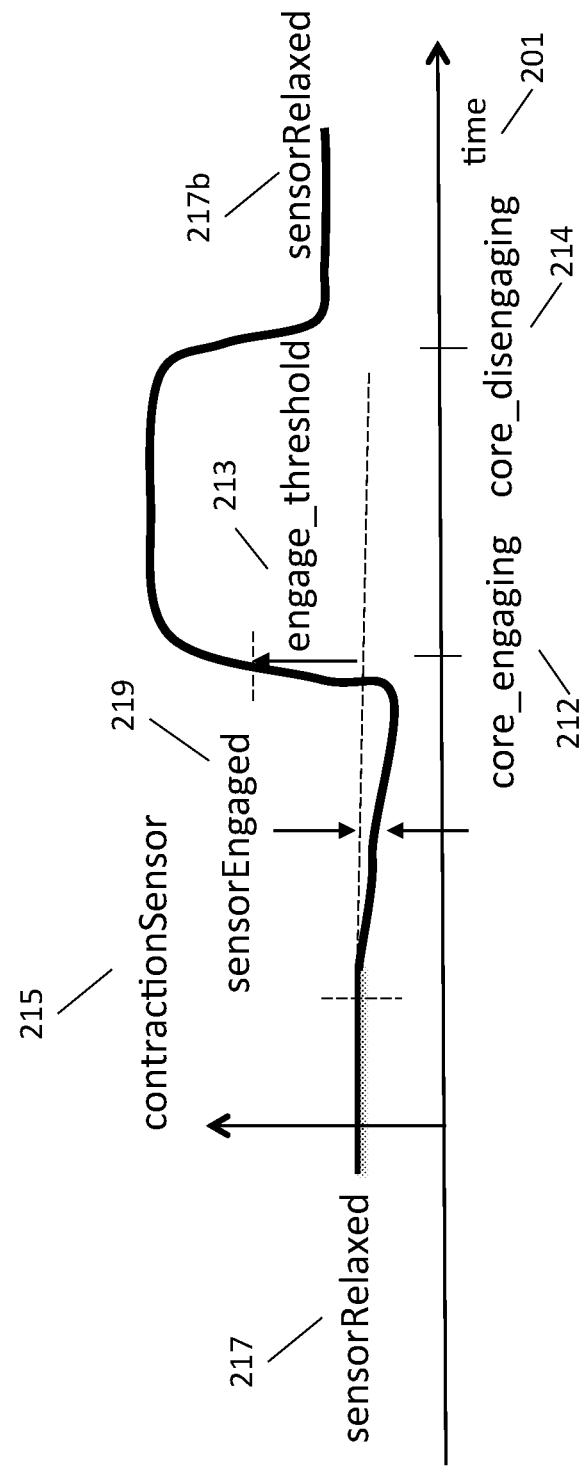
FIG. 19 illustrates features of the signal received from a contraction sensor for identifying a core engagement.

In an embodiment, the core engagement identification algorithm may track a current relaxed value of the core and changes from this value. Referring to FIG. 19, let us refer to the instantaneous value of the contraction sensor value as contractionSensor 215 (vertical Y-axis) plotted as a function of time 201 (horizontal X-axis) starting with the core relaxed. The core contractionSensor 215 then reduces in value prior to increasing during a core engagement. Some users may move their core section such that the pressure on the contraction sensor moves first in the opposite polarity before moving in the polarity of their engaged core, resulting in the contractionSensor 215 shape shown in the figure. This may result from different ways a user may engage his or her core. For example, a user may slightly firm or contract the core muscles, pulling the contraction sensor gently in before firming and pushing slightly outward. This embodiment of core contraction detection processing handles many possible core contraction situation sequences effectively.

Let us refer to the value of contractionSensor 215 when the core is relaxed as sensorRelaxed 217. Let us refer to the deviation of contractionSensor 215 away form sensorRelaxed 217 as sensorEngaged 219. The value of sensorEngaged 219 is referenced to the value of sensorRelaxed 217. In an embodiment, these parameters may be related through the equation:

contractionSensor=sensorRelaxed+sensorEngaged.

When sensorEngaged 219 equals zero, sensorRelaxed 217 equals contractionSensor 215. Finally, engage_threshold 213 may be defined as the threshold for sensorEngaged 219 that when equal to or exceeded, the core is identified as engaged and when not exceeded, the core is identified as relaxed. Since in this embodiment, sensorEngaged 219 is referenced to sensorRelaxed 217 before changes in sensorEngaged 219 occur, it allows different paths or trajectories for sensorEngaged to exceed the engaged threshold 213

Figure 20:
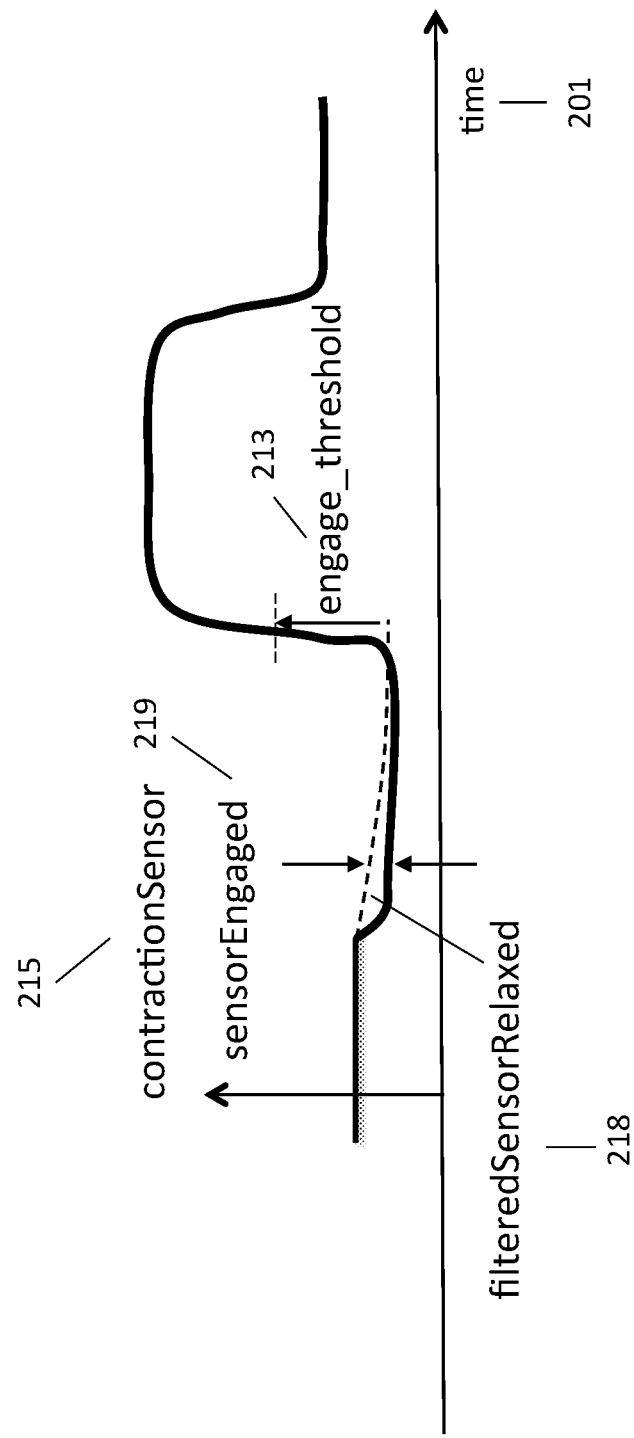
FIG. 20 illustrates filtering the contraction sensor value when the core is relaxed.

Referring to FIG. 20, an embodiment is illustrated where contractionSensor 215 (vertical Y-axis) is plotted as a function of time 201 (horizontal X-axis). During the time the core is identified as relaxed, contractionSensor 215 is passed through a filter. The filter output is filteredRelaxedSensor 218. Parameter engage_threshold 213 is then added to filteredRelaxedSensor 218. When sensorEngaged is equal to or exceeds engage_threshold 213, the core is identified as engaged. In an embodiment, the filter may be implemented as a signal processing block that may include a lowpass filtering to reduce high frequency transients. The signal processing block may included linear or non-linear filtering. Other non-linear signal processing techniques may be utilized.

For some applications, design of the filter may pose a difficult and non-obvious challenge. The wider the filter bandwidth, the better the filter output may track transients due to body movement. But it may also be difficult to differentiate between a movement transient and a valid core engagement. Some users may take longer to engage their core. Some may be fairly quick to engage their core. As mentioned earlier, some may move their core inward before firming. This may reduce the effectiveness of this approach to be effective for a broad range of user variability. In an embodiment, this may be addressed with a programmable or adaptive filter. Later in this description, we will present a different embodiment to address tracking body movements when the core is relaxed.

Using the wearable device described in U.S. patent application Ser. Nos. 14/132,808, 14/789,136, 14/652,542, and 14/817,964, adjustment parameters for the device on a user in an appropriate sensing position include belt adjustment and bumper height. The belt may be adjusted to result in a firm, yet comfortable fit on the user. The bumper height may be adjusted to press through body fat or clothing to the underlying muscle. A user with a higher degree of body fat or a less developed muscle may benefit from a higher bumper height.

It may be beneficial to provide the user with quantifiable measures to help with adjusting both the belt tightness and bumper height. Quantitative measures may be provided to the user through an app running on a smart device via a display or speaker on the smart device. These measures may be provided by the core engagement identification algorithm to aid in the adjustments of both the belt and bumper.

In an embodiment, parameters sensorRelaxed 217 and sensorEngaged 219 from the core engagement identification algorithm may be utilized to aid in belt and bumper adjustment through the app. Parameter sensorRelaxed 217 may be utilized for belt adjustment. A recommended belt adjustment range may be identified by the app and output to the user through the user interface. If sensorRelaxed 217 is less than the lowest value of the belt adjustment range, the recommendation may be to tighten the belt. If sensorRelaxed 217 is above the top of the range, the recommendation may be to loosen the belt. Once sensorRelaxed 217 is in the appropriate range, sensorEngaged 219 may be used to adjust the bumper height. The user may be recommended to place the device over an appropriate area to monitor the core muscles using the smallest available bumper. In the case where a mushroom cap 203 or a similar component is available, it may be used. The user may then engage their core muscles and observe sensorEngaged 219. If sensorEngaged 219 is larger than a target, no changes may be needed to the bumper. If the target cannot be met with a comfortable degree of core contraction, then a bumper extender may be recommended. The user may be informed of multiple alternative locations that may be appropriate for core contraction sensing by the app through a user interface output such as a visual display. Furthermore, the app can also recommend that the user work with a licensed physical therapist or physician, or certified fitness trainer for coaching and guidance. If the bumper height is changed during this fitting procedure, the belt adjustment procedure should be repeated prior to checking the new bumper height.

Let us further examine possible features of the core contraction identification algorithm implementations. A summary of desirable elements and design challenges with implementing a core engagement identification algorithm may include the following:

1. Engage threshold tracks the relaxed core value so the change in pressure on the contraction sensor from an engaged core triggering a positive core engagement identification is relative to the relaxed core value (met using sensorEngaged 219);

2. Engage threshold may be user adjustable or identified via a calibration procedure (met using engaged_threshold 213);

3. When the core is relaxed, the algorithm may get stuck in a condition that even valid core contractions do not move the algorithm to a condition where identifying a core contraction is possible with normal usage; provision is needed to exit this condition using a reset;

4. When the core is relaxed but the algorithm identifies the core as being engaged, the algorithm may get stuck in that condition and not recover with normal usage; provision is needed to exit this condition using a reset;

5. When the device is first placed on a user, the algorithm may get stuck in an undesired state requiring a reset; a button or switch on the wearable to implement the reset may be undesirable; provision is needed to exit this condition using a reset;

6. Efficient way to report sensorRelaxed and sensorEngaged to the user through the app;

7. Desirable to identify core engagement that increases the pressure on the contraction sensor as well as core engagement that decreases the pressure on the contraction sensor (support bracing and hollowing);

8. Desirable to identify when the core is engaged and when it is relaxed to allow duration of a core engagement to be measured;

9. Provision to provide a sound or buzz upon core engagement; the same or another identifiable sound or buzz during the core engagement; and a same or another identifiable sound or buzz during the core disengagement, that is, as the core transitions from the engaged to the relaxed condition;

10. While a user has their core engaged and performs a movement, the movement of the wearable device may result in changes in pressure on the contraction sensor during the movement; these changes in pressure may result in a disengage; and 11. Accommodate various ways a user may transition from a relaxed core to an engaged core.

In an embodiment, the derivative of contractionSensor at time n can be defined as $$derivContractionSensor[n]=contractionSensor[n]-contractionSensor[n-1]$$

If we sum derivContractionSensor[n], we are effectively observing only changes in the contractionSensor from the time index we begin the summation.

In one embodiment, when the core is identified to be relaxed, we may begin the summation, and the result may be sensorEngaged[n] which is sensorEngaged 219 at time index n wherein:

$$sensorEngaged[n] = \sum_{k=Start_{Relaxed}}^{n} derivContractionSensor[k]$$

This implementation of sensorEngaged[n] 219 may have desirable qualities. As described earlier, the sensorRelaxed 217 is removed from the contractionSensor 215 so only changes from sensorRelaxed 217 are tracked. A second desirable quality is that sensorEngaged 219 may be reset back to zero at any time. Therefore, if a change in sensorRelaxed 217 occurs, by starting the summation at the time instant that the new relaxed value is identified, the sensorEngaged 219 may be evaluated relative to this new value of sensorRelaxed 217.

Referring to FIG. 19, we may refer to the time index where sensorEngaged equals or exceeds engage_threshold 213 as core_engaging 212 wherein the user's core is identified as being engaged 203. Similarly, when the user's core is engaged 203, we may refer to the time index where sensorEngaged 219 reduces below engage_threshold 213 as core_disengaging 214 wherein the user's core is identified as being relaxed 205. After sensorEngaged 219 reduces below the engage_threshold 213 the muscle being monitored will reduce in firmness until it reaches the relaxed condition. The result is contractionSensor 215 will decrease and at a time sample, will stop decreasing. Alternatively, contractionSensor 215 may decrease beyond the point that sensorEngaged 219 equals zero and then increase back to a relaxed state sensorRelaxed 217b where this value may be different from sensorRelaxed 217 before the core engagement. In other words, contractionSensor 215 may overshoot sensorRelaxed 217b and bounce back. By monitoring contractionSensor 215, we may identify the core to be relaxed 205 when the current value contractionSensor[n] 215 is greater than or equal to the previous value contractionSensor [n−1] 215.

In an embodiment, after the core muscles are relaxed and the core_disengaging 214, and contrationSensor 215 returns to an identified relaxed value sensorRelaxed 217, we may update the value of sensorRelaxed using the equation:

$$sensorRelaxed=contractionSensor-sensorEngaged.$$

In an embodiment, when the relaxed condition is identified, sensorEngaged 219 may be reset to zero, and sensorRelaxed 217 may be initialized to contractionSensor 215. This may result in sensorRelaxed 217 tracking changes in the relaxed value due to body movements and positioning from before a core engagement to after a core engagement.

In an embodiment, the engage_threshold 213 may be adjustable. The parameter engage_threshold 213 may be adjustable through the app. In an embodiment, an effective value for engage_threshold 213 may be identified via an auto-calibration procedure. The user may select a page in the app for auto-calibration of engage_threshold 213. A button on the GUI for the app may be touched to begin the auto-calibration routine. The user may be advised to begin with the core in the relaxed condition. Then, the app may instruct the user to transition the core to the engaged condition, held in the engaged condition for a specified time interval. For example, two seconds, then transition the core back to the relaxed condition. This sequence of transitioning the core from relaxed to engaged, and back to relaxed may be performed one or more times. If more than one sequence is advised and the core contraction signals during the calibration process can be monitored and observed by the app. With this core contraction calibration information, techniques such as averaging may be utilized. The app may identify a minimum value and a maximum value of contractionSensor 215. The minimum value may be identified as sensorRelaxed 217 and at the maximum value of contractionSensor 215, the difference between contractionSensor 215 and sensorRelaxed 217 may be identified as sensorEngaged 219. A predetermined fraction of sensorEngaged 219 signal value may be identified as engage_threshold 213. For example, in an embodiment fifty percent of sensorEngaged 219 may be identified by the app as the engage_threshold 213. In an embodiment in which multiple sequences are advised, for example, five trial sequences, the average value of multiple engage thresholds 213 calculated during each core contraction calibration sequence may be stored and utilized by the app to determine the engage_threshold 213. In an embodiment, outlier values may be identified and removed from the evaluation. In an embodiment, if the values do not meet a certain criteria, for example, if the calculated values of engage_threshold 213 are below a minimum value, the user may be advised to repeat the calibration procedure. This process may allow other techniques and methods to be utilized to identify an appropriate value for engage_threshold 213. In an embodiment, the calibration procedure may be utilized to identify a starting value for engage_threshold 213 and the user may then modify this value via the app as part of a fine tuning procedure. Other heuristics may be utilized for different applications to determine the engage_threshold 213.

User experience or the perception a user has about the wearable device and the app is a critical consideration in development of the device, app, and algorithms that operate on the sensor data. It is important that the user perceive that the information being provided from the sensor data is accurate. To this point, it is critical that the algorithms minimize the instances in which the algorithms themselves may modify data as though operating on its own. In an embodiment, if the firmness of the muscles being monitored are not changing, the outputs of the core contraction algorithm should not be changing. However in some instances, it may be acceptable for the algorithm to make changes when the muscles are not changing. These instances may include situations where the algorithm is stuck in a state that normal use is not able to recover from. In an embodiment, when such instances may be identified, automatic or timed resets may be utilized. In these embodiments, calculating sensorEngaged 219 using the numerical summation algorithm by the app is convenient as it allows a reset to be implemented simply by resetting the summer to a known value. In some applications, the reset value may be zero.

As described in the other patent descriptions, the wearable device may be worn on an elastic belt. A user may place the wearable device into position over, for example, a core muscle, and let the elastic belt pull the device toward the body and into place. This may result in the device striking the body with a mild slap and cause a transient step on the contraction sensor. This step may be very large in magnitude and may place the algorithm parameters in relationships to one another or to values that keep normal operation from proceeding. In cases where the relationships of the parameters can be identified in unwanted states, the algorithm may reset sensorEngaged 219. A reset may include setting sensorEngaged 219 to zero and equating sensorRelaxed 217 to contractionSensor 215.

In an embodiment, when a user detects that the algorithm is in a stuck state and the parameters are not as expected, for example if sensorEngaged 219 is not zero when the core is relaxed, a manual reset may be implemented. It may be desirable to use the already available sensors on the device to implement the manual reset instead of requiring the addition of a switch or button. This may be implemented in a number of ways, depending on which sensor is utilized. In an embodiment, the user may firm their core and press and release on the device a number of times. For example, the user may press and release three times in succession. The algorithm may have a section of code designed to observe successively large and small values of contractionSensor 215. When a number, for example, three sets of large and small values are identified within a fixed period of time, for example one second, the app may cause a reset to occur.

When the core is in the relaxed condition and user moves, as described earlier, this may result in changes to sensorRelaxed 217. It may be desirable to have sensorEngaged 219 near a value of zero when the core is relaxed to maintain the required change on the contraction sensor greater than engage_threshold 213 to result in the identification of an engaged core. After a core engagement, sensorRelaxed 217 may settle on a value and sensorEngaged 219 may be equal zero. If the user's body moves, for example, suppose the user is seated and then leans forward, the sensorRelaxed 217 value may stay the same but sensorEngaged 219 may change to a non-zero value. If the user stays in that position, sensorEngaged 219 may maintain the non-zero value. If this condition persists, it may be desirable that the app perform a system reset to return sensorEngaged 219 back to zero. In an embodiment, the algorithm may observe the contractionSensor 215 value and identify when it stays within a range of values, for example, plus or minus one for a time period, for example, two seconds; when both the range and time period requirements are met, a reset may be triggered by the app. Since this reset may occur when the core is relaxed, this reset may be referred to as a Relaxed Reset. Both the range and time period may be fixed, adjustable, or they may be a function of the sensorEngaged 219 value at the start of an evaluated time period. In an embodiment, a lookup table may be used to identify the range and time period to be used for Relaxed Reset as a function of sensorEngaged 219. In an embodiment, Relaxed Reset may be turned on or off through the app and values for range and time period may be adjustable in the app.

When the wearable device is mounted on a user and the user moves or a movement happens such that a core engagement is identified by the algorithm and the user's core is in the relaxed condition, the identification of a core engagement may incorrectly occur and persist indefinitely. In one embodiment, when core_engaging 212 is identified, a timer begins counting. When a time limit is reached, a reset may be triggered by the app. Since this reset occurs when the core is identified to be engaged, this may be referred to as the Engaged Reset. In an embodiment, Engaged Reset may be turned on or off through the app and values for the time limit may be adjustable in the app.

In an embodiment, a settings parameter may be used to select between identifying a core contraction as when sensorEngaged 219 exceeds a positive engage_threshold 213 or when sensorEngaged 219 decreases below a negative value of engage_threshold 213. Exceeding a positive engage_threshold 213 has been called bracing in earlier patent descriptions. Decreasing below a negative engage_threshold 213 has been called hollowing in earlier patent descriptions. The algorithms described in this description are mainly described from the perspective of bracing core engagements. They can easily be modified to support hollowing.

In applications where core engaging 212 and core disengaging 214 are identified by the app which then, provides feedback to the user at the beginning of a core engagement (core engaging 212), at the end of a core engagement (core disengaging 214), and during a core engagement 203 (between core engaging and core disengaging) may be facilitated. In one embodiment, the app and buzzer and sound devices on the wearable may be programmed to provide feedback to the user by identify core engaging 212, core disengaging 214, and core engaged 203 independently with different sounds, buzz patterns, or beep patterns. The feedback signal for each aspect of the core engagement may be turned off and on independently. For example, the user may desire to have only the app provide a beep on core engaging 212 and be silent otherwise. In another instance, the user may desire to have the wearable device provide a single buzz on core engaging 212, and two short buzzes on core disengaging 214. Other combinations of feedback may be used, depending on the preferences of the user.

In an embodiment, a counter may be shown on the app to provide a core contraction and/or timing count. For example, the app may provide a core contraction recording and monitoring in seconds starting on core engaging 212 and ending on core disengaging 214. This may provide a feedback from the app to the user showing how long an individual core engagement may have lasted through a system output such as a GUI. Providing the feedback of the duration of core engagements may be part of a practice routine provided by the app to the user.

As a user performs a dynamic movement such as standing up from a seated position with an engaged core, core_disengaging 214 followed by core_engaging 212 may occur during the movement. The incorrect identification of core_disengaging 214 followed by core_engaging 212 may be confusing or irritating to the user, especially if the user receives two successive core_engaging 212 signals from the app or device when the core was engaged throughout the movement. This transient may occur if the contraction sensor 175 moves away from and back toward the body during the movement, if underlying muscles move during the movement causing a short drop in incident pressure on the contraction sensor 175, or from another short transient causing a short pressure drop. In an embodiment, the body movement sensors may set a body moving flag on a visual display output when the body is identified to be moving in a manner known to create this transient. The body moving flag may be used to inhibit the effect of the core_disengaging 214 signal while the flag is set. This may eliminate the effect of this undesired transient that may occur during a movement like standing up from a seated position.

The body moving flag may be set or body movement may be identified when the output of an accelerometer or gyro signals transmitted to a processor and processed by the app exceeds a predetermined or algorithm calculated threshold value. In some applications, the first or second integral of the accelerometer output or the first integral of the gyro output may be used to minimize false triggers and identify valid movements. In other applications, other signal processing techniques may be used on the movement sensor outputs to identify specific types of body movements.

Many core strengthening exercises, for example, planks, are performed preferably with little or no torso movement. One way a person may perform planks is to lie face down, place each hand thumbs up just under each respective shoulder, with elbows tucked close to the body, then contract the core region and balance on the toes, and elbows and forearms. This position with engaged core muscles may help to develop the core muscles that wrap around the region of the lumbar spine. A person may be encouraged to develop the ability to hold this position for many tens of seconds. Engaged Reset may not be useful in this app because having a time limit of, for example, 30 seconds may make Engaged Reset of little value. In an embodiment, Engaged Movement Reset may be utilized where a reset is triggered when the core is identified to be engaged and a body movement is identified by the movement sensors. Using Engaged Movement Reset, if the algorithm gets stuck in an engaged condition, any appreciable body movement may trigger a reset. In an embodiment, the threshold for identifying a body movement may be adjustable through the app.

In an embodiment, when a button is touched in GUI of the app, a reset may be triggered. In the app, a concise implementation of a reset button, a measure of sensorRelaxed 217, and a measure of sensorEngaged 219 may be desirable as these three items may be present on many pages of the app. Parameters sensorRelaxed 217 can quickly inform a user if the device belt tightness is appropriate, and changes in sensorEngaged 219 when the core is engaged may provide feedback about positioning of the device. A reset button actuation can allow the algorithm to be reset simply with the touch of a button. In FIG. 21a-FIG. 21c, different embodiments of these three items are shown. By placing the items within the area of the button, efficient use of visual space on the app GUI may be achieved. In the embodiment shown in FIG. 21a, a rectangular button 251 is shown. Touching anywhere on the rectangle may trigger a reset. Also shown are numerical values for sensorRelaxed (value "91") 253 and sensorEngaged (value "0") 255. In a second embodiment shown in FIG. 21b, a rectangular button is again shown. In this embodiment, a bar slider 265 is used to represent sensorRelaxed 217. Two light vertical tick marks 261, 263 are shown. These may represent the boundary for acceptable tightness of the belt. The thick vertical line represents sensorRelaxed 217. The thick line may move to the left as sensorRelaxed 217 decreases and move to the right as sensorRelaxed 217 increases. If sensorRelaxed 217 is outside the range defined by the two light vertical tick marks 261, 263, the user may be advised to adjust the belt tightness. If sensorRelaxed 217 is to the left of the left most light vertical tick mark 261, the user may be advised to tighten the belt. If sensorRelaxed 217 is to the right of the right most light vertical tick mark 263, the user may be advised to loosen the belt. The number "0" 255 may represent sensorEngaged 219. In another embodiment, the reset button is round as shown in FIG. 21c and FIG. 21d. Touching the circle 251 will trigger a reset. As the core is engaged, in one embodiment, the radius of the circle may increase and the color 267 may change as indicated by the dotted pattern. One or both of these changes to the circle may be used to illustrate the identification of an engaged core through the GUI to the user. The sensorRelaxed 217 value is again shown on the slider 265 similar to the configuration of FIG. 21b.

In an embodiment, sensorRelaxed 217 and sensorEngaged 219 may be presented to the user in the app as a color or gray shade changes of an element, on sliders, as numbers, element size changes, or may use another visual, audible, or other tactile means of providing feedback. These embodiments illustrate inventive presentations of some of the critical parameters from monitoring the core that may be used to provide feedback to the user. Additional parameters may be added to similar features for different applications.

Figure 22:
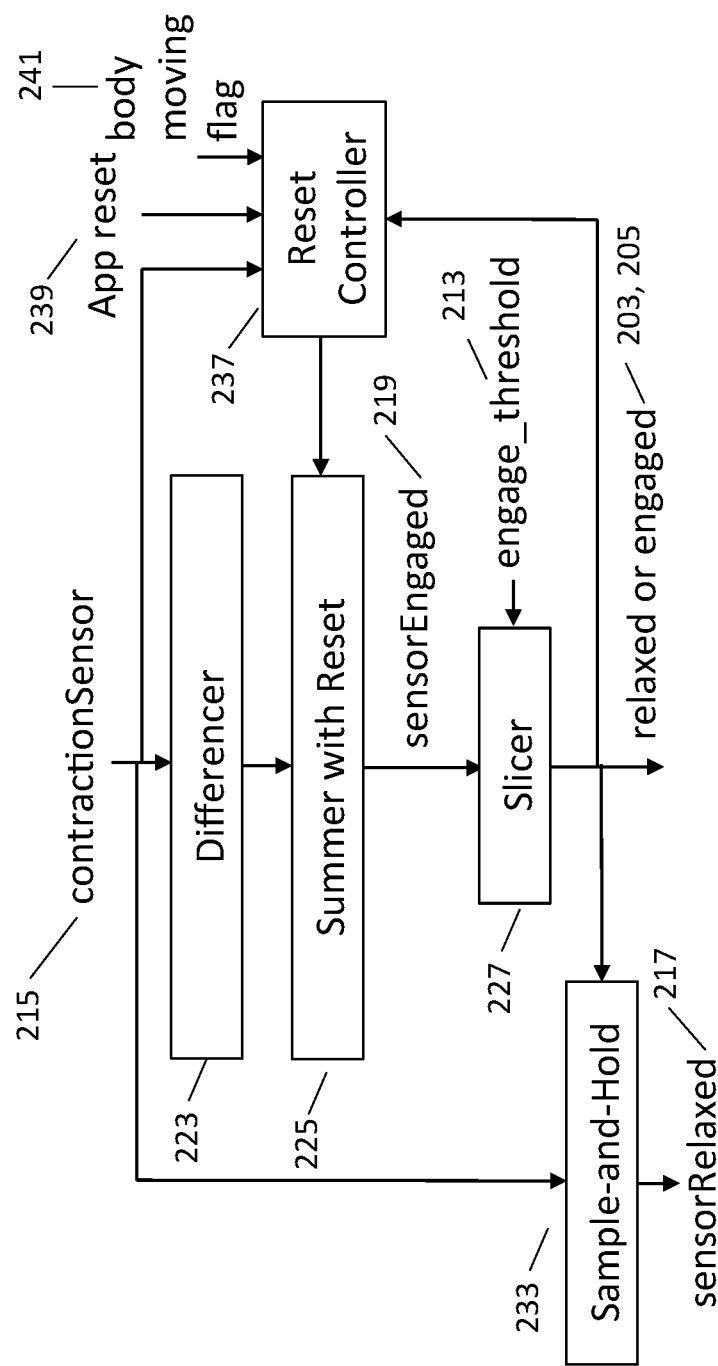
FIG. 22 illustrates a signal flow graph for the core engagement identification algorithm.

A signal flow diagram for an embodiment of the core contraction algorithm is shown in FIG. 22. Data from the contraction sensor contractionSensor 215 is the input. The system may be configured so that when the pressure increases on the contraction sensor, contractionSensor increases.

The Differencer 223 block generates the difference between the current contractionSensor[n] and the contractionSensor[n−1]. The difference samples are input to the Summer 225 block. The output of the Summer 225 block is sensorEngaged 219. The Summer 225 may be reset by the output of Reset Controller 227. When sensorEngaged passes through the engage_threshold 213, Slicer 227 identifies core_engaging 212 and the core is identified as engaged. From the engaged condition, when sensorEngaged 219 goes negative and passes through the engage_threshold 213, core_disengaging 214 is identified and the core is identified as relaxed. When the core first returns to relaxed, sensorEngaged 219 is reset to zero and the value of contractionSensor 215 is sampled and held by the Sample-and-Hold 233 block. The output of the Sample-and-Hold block 233 is sensorRelaxed 217.

There can be a number of inputs to the Reset Controller 237. The input data contractionSensor 215 is input directly and may trigger a reset when in one embodiment, the user engages the core and presses and releases quickly three times. This is one of many ways, the user may perform a manual reset. The app may have a button 251 displayed on a GUI that when touched may trigger a reset. The relaxed 203 or engaged 205 condition may be an input to the Reset Controller 237. When in the relaxed 203 condition, a Relaxed Reset may be selected to occur. A Relaxed Reset may be triggered when the core is in the relaxed condition and contractionSensor 215 stays within predetermined value limits for a predetermined time period, both of which may be user specified through an input to the app. When in the engaged 205 condition, an Engaged Reset may be selected to occur. An Engaged Reset may be triggered after the core is engaged 205 for a time limit, which may be user specified. In an embodiment, both the Relaxed Reset and the Engaged Reset may be turned on or off via the GUI of the app. In an embodiment, when the body is identified to be moving via the movements sensor and movement sensor algorithm, a body moving flag 241 may be set and core_disengaging 214 may be muted until the body moving flag is reset. This may be used to keep the core_engaging 212 signal from signaling twice during a single movement such as standing up from a seated position.

The signal flow diagram in FIG. 22 is merely an example of an embodiment of a signal flow diagram utilizing the inventive concepts presented in this description.

In an embodiment, functional modes may be defined. Functional modes may be distinguished by a number or name. When a functional mode is selected, preset programmable configurations of the core contraction algorithm may be selected. In an embodiment, modes are numbered. In this embodiment, in Mode 1, Relaxed Reset and Engaged Reset may be turned off. Use of the body moving flag 241 may also be turned off. In Mode 2, both Relaxed Reset and Engaged Reset may be turned on and the timers may each be set for 2 seconds. Use of the body moving flag 241 may be turned off during Mode 2. In Mode 3, the Reset conditions of Mode 2 may be turned on, and use of the body moving flag 241 may also be turned on. Functional modes may make it simpler for the user to change programmable parameters based on specific use models. Settings may be selected to provide the user with an appropriate selection of parameters for specific activities. In an embodiment, the user may be allowed to modify parameters after a mode is selected.

In an embodiment, sensorRelaxed 217 may be presented to the use as a color or gray shade, or on a slider on a visual display of a GUI of the app, or using another visual, audible, or other tactile means of providing feedback. In an embodiment, sensorEngaged 219 be presented to the user as a number, or on a slider, or changing the radius of a circle, or may use color or gray shade on an illustration, or use another visual, audible, or other tactile means of providing feedback.

The wearable device may connect to a smart mobile computing device such as a smart phone, smart pad, PC, or dedicated device running an app. The app may run on the iOS or Android operating system, or it may run on a proprietary operating system. The app may be part of the app used to control the parameters of the wearable device and receive data and provide feedback from the device. The app can be used to play back music. A song or piece of music is made up of musical notes and each of the musical notes has a pitch and duration. The pitch is related to the primary frequency of the note and the note pitch is defined by the location of the note on the staff.

Figure 23A:
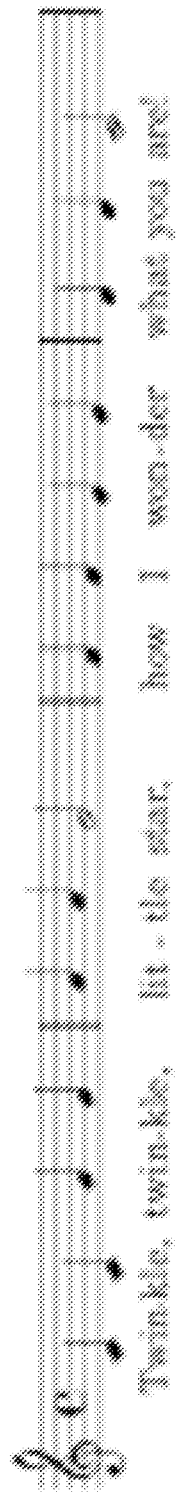
FIGS. 23a and 23b illustrate music and notes that can be used with the inventive system.

With reference to FIG. 23a, a portion of music and lyrics in a traditional form with musical symbols with staff, bar lines, G clef, and notes are illustrated from the song Twinkle Twinkle Little Star. The first note in the first "Twin" above is middle C on the piano. The duration is related to how long the note lasts. The duration is indicated by the shape of the note on the staff. A solid oval with a protruding line on the right is a quarter note which lasts for one beat. In contrast, a hollow oval with a protruding line on the right is a half note which lasts for two beats. Notes may be played on different instruments, resulting in a different sound or timbre.

Figure 23B:
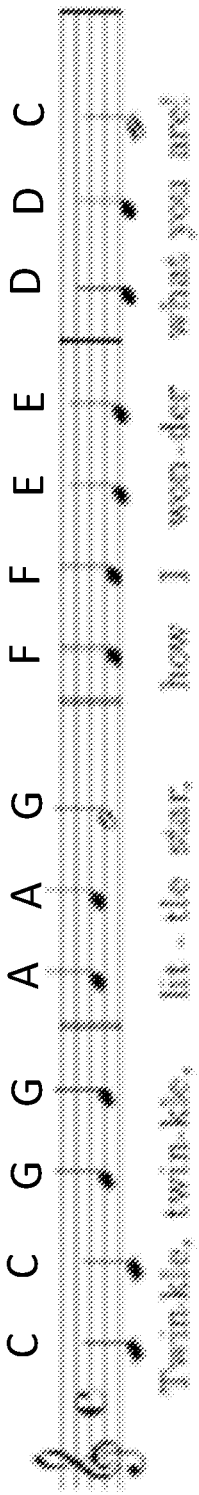

With reference to FIG. 23b, the letter note designations for the notes on the staff are illustrated above each of the notes. In this example, the notes are designated by the letters C, G, A, F, E, and D. These names may correspond to the note pitch but not indicate the note duration. There are different ways the sound of a particular instrument may be played electronically. Sound samples or synthesis are two possible ways that sound can be played electronically by the app on the mobile computing device.

The mobile app can store the song in memory and provide the audio output and visual display necessary to practice timing core contractions with the tones of the music in various ways. The sequence or order of notes in a song may be stored in a file on the smart mobile computing device. The playback sound may be generated using synthesis or an instrument sample or some other means. The songs stored on the mobile computing device may be familiar to the user allowing the user to know the duration of each note. The user interface of the app may allow the user to select a song with which to exercise the practice of performing core contractions. Once a song is selected and the "play song" portion of the app is started, the smart device may begin to receive data from the core contraction sensor on the wearable device In an embodiment, every time the user engages their core and the engagement is detected by the device and/or the smart phone app, a note may sound from the stored song and the duration of each note may be determined substantially by the duration the user holds their core in the engaged (or contracted) state. The notes may be sounded in sequence as defined in the electronic song file.

Figure 24B:
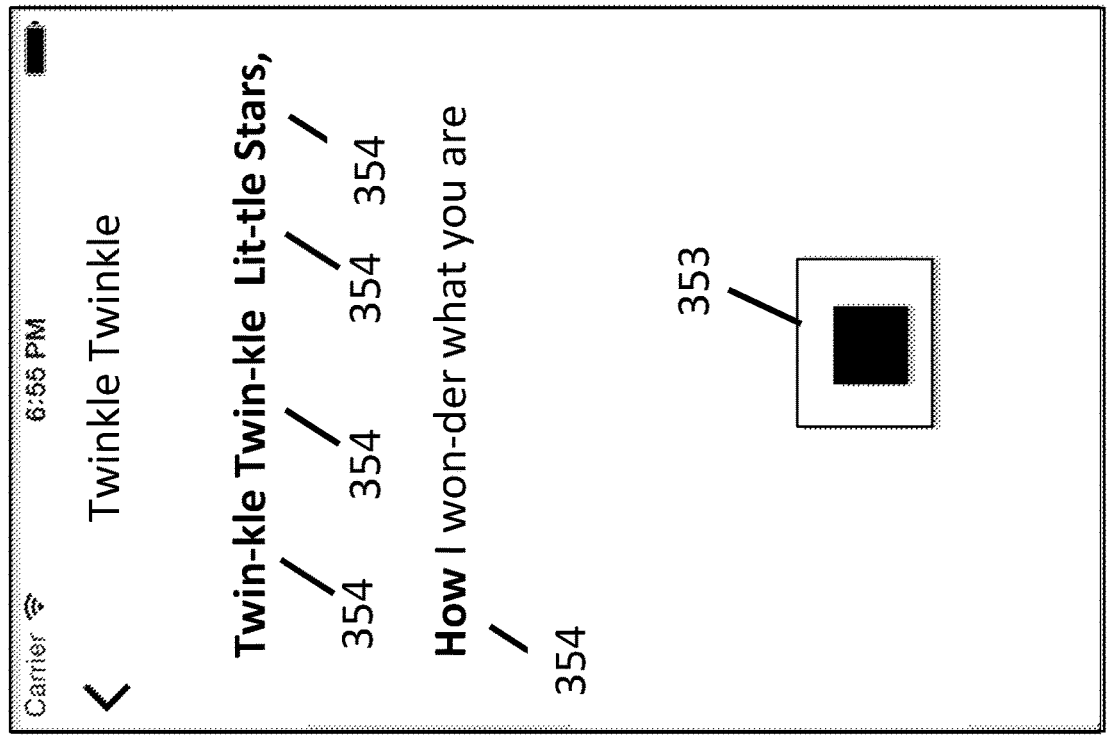
FIG. 24a-24d illustrate embodiments of user interfaces on a computing device display.
Figure 24A:
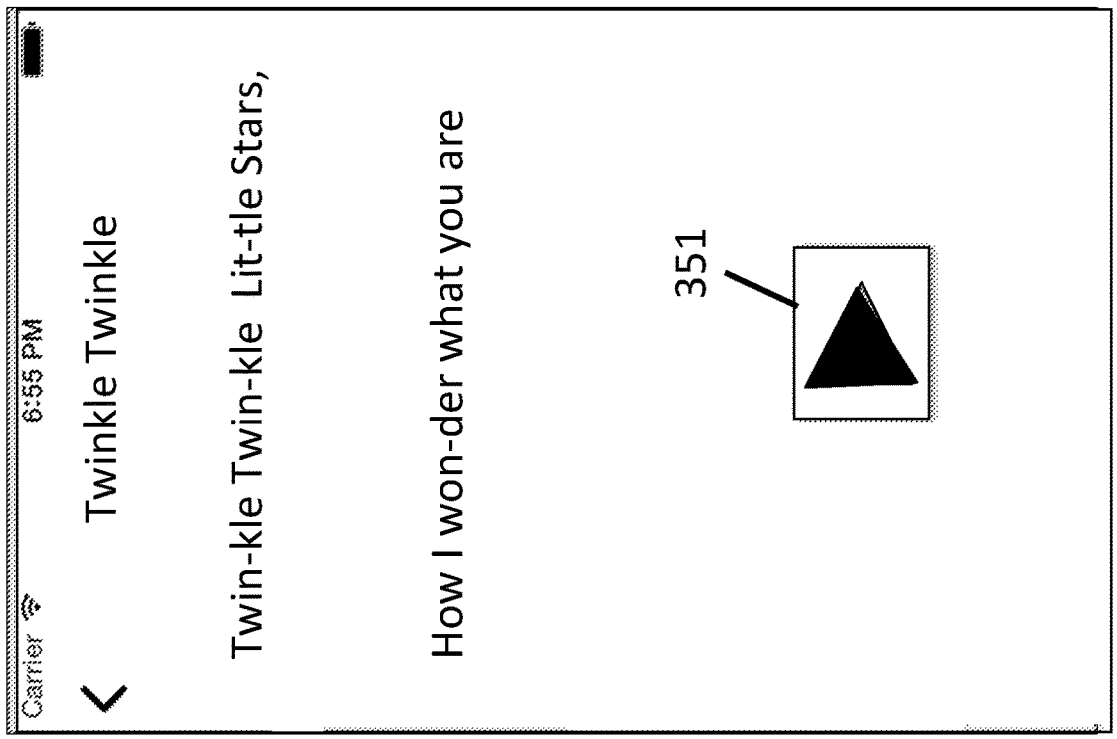

For example, with reference to FIG. 24a, in an embodiment, the App may display the name of the song and the lyrics with a play button. When the user wishes to start the song, the user can press the play button 351 with triangle play symbol. By using songs that are familiar to a user, the desired relative duration of most of the notes will be known to the user. Therefore, no real musical notation may be needed. The app can readily be used by user's not familiar with musical notation. Musical notation including notes with pitch and duration may also be displayed on the mobile computing device. For example, in the current example where Twinkle-Twinkle is well known by many people in the US, simply having the words of the song shown in the app may allow a user to play notes with the correct or desired duration.

With reference to FIG. 24b, the app will proceed to play the song and display the name of the song and the lyrics. Once the start button it touched, each time the user engages their core, a note will sound. The note duration will be substantially proportional to the duration that their core is contracted. The start button may turn into a stop or pause button 353 during the song playing with the square pause symbol. Words corresponding to notes that have already been sounded may change color or font style. Referring to the figure, the words up through the word "How" are shown in bold 354, indicating they may have sounded. The mobile computing device will also receive core contraction signals from the core contraction sensor in the wearable device. As the song progresses, the displayed lyrics can change in synchronization with the music.

Figure 24C:
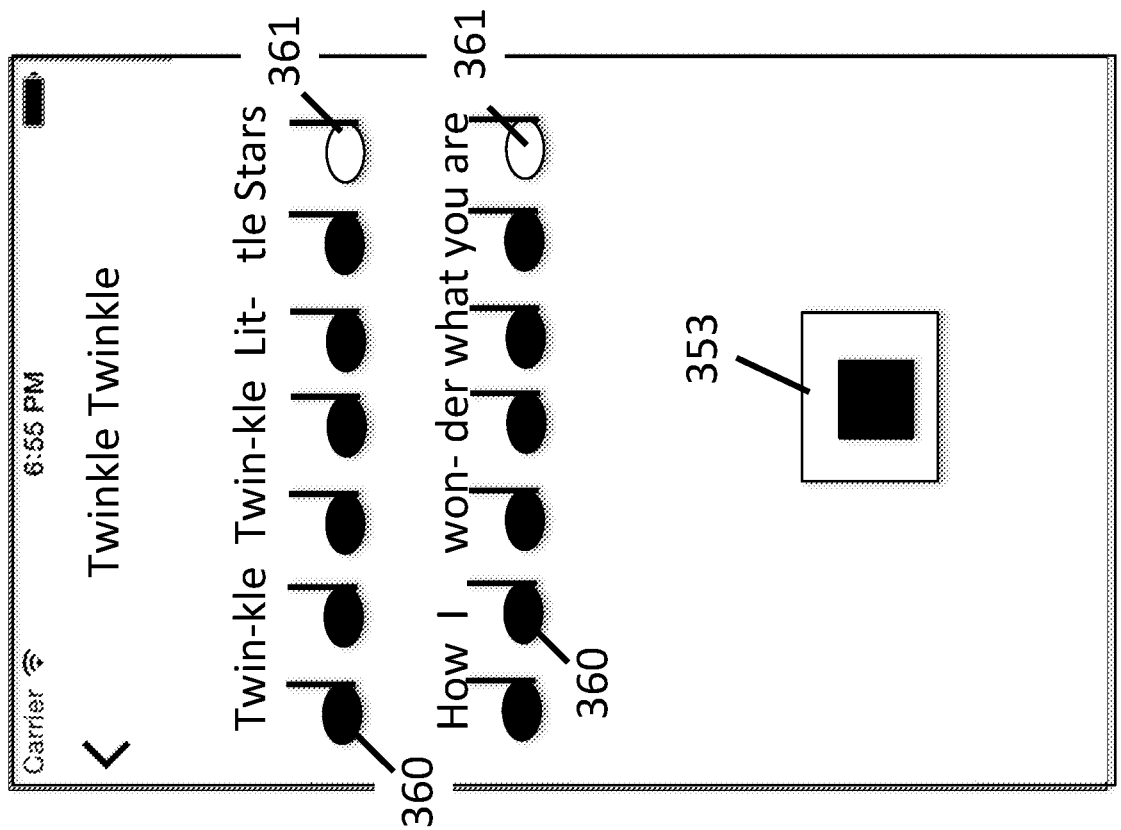

In an alternative embodiment, with reference to FIG. 24c, the app will proceed to play the song and illuminate notes that correspond to the song as they are played. In this example, most of the notes are quarter notes 360 designated by the solid black, but the notes under "Stars" and "are" are half notes 361 designated as being longer in duration by the hollow note. Note durations may be shown as indicated in the figure. However, if the song is well known, the not and duration may not be needed. Other indicators such as numbers corresponding to the number of beats in the note. For example, 1 for quarter note, 2 for half note, etc. may be used.

Figure 24D:
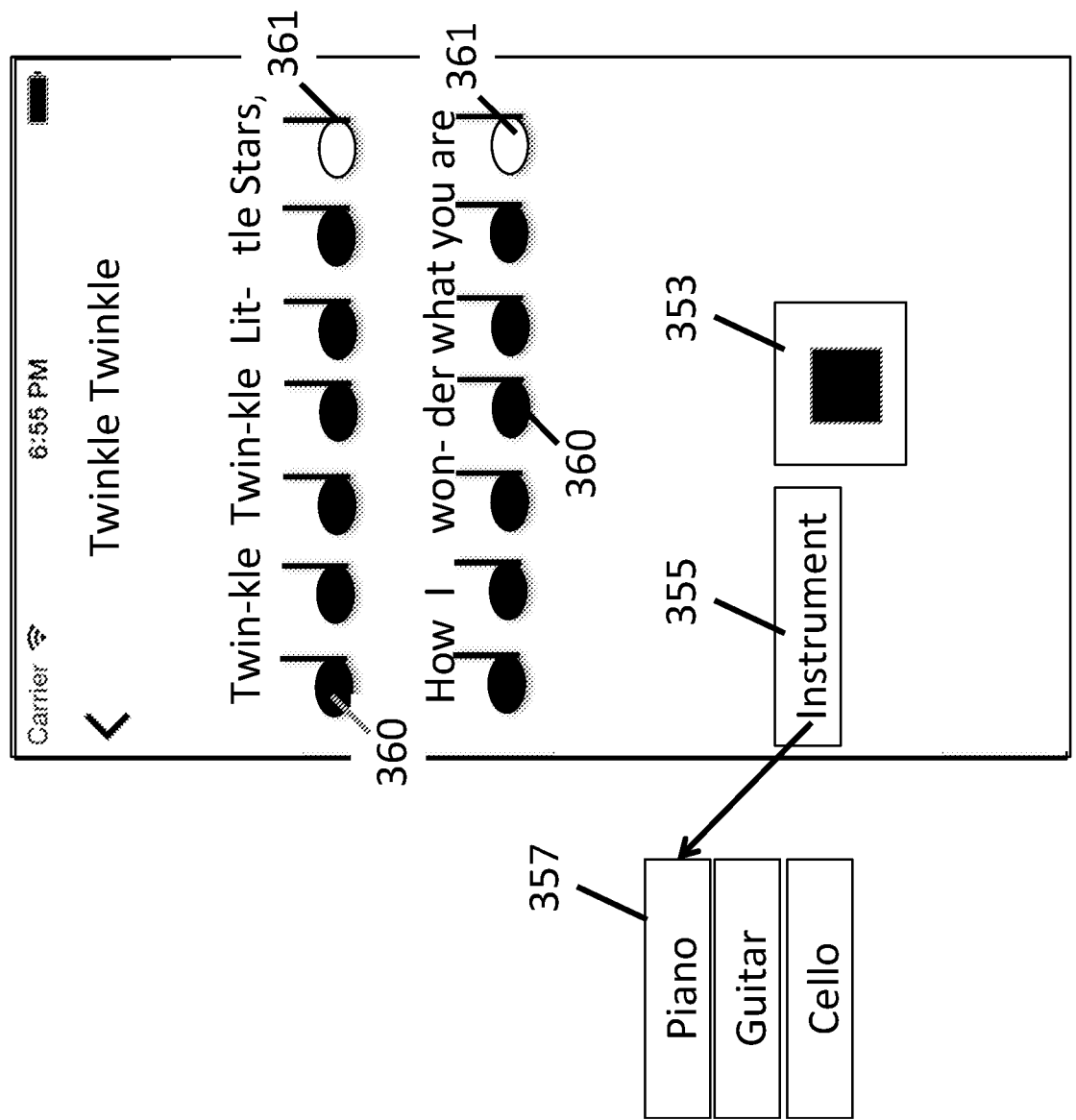

In an embodiment, the user interface of the app can allow the user to select the type of instrument that may be sounded as the song is played. With reference to FIG. 24d, the user interface can have a pull down menu 357 with a plurality of instruments 355. In this example, the possible instruments include: Piano, Guitar, and Cello. By touching an icon or word, one of a number of possible instruments may be selected.

Figure 25A:
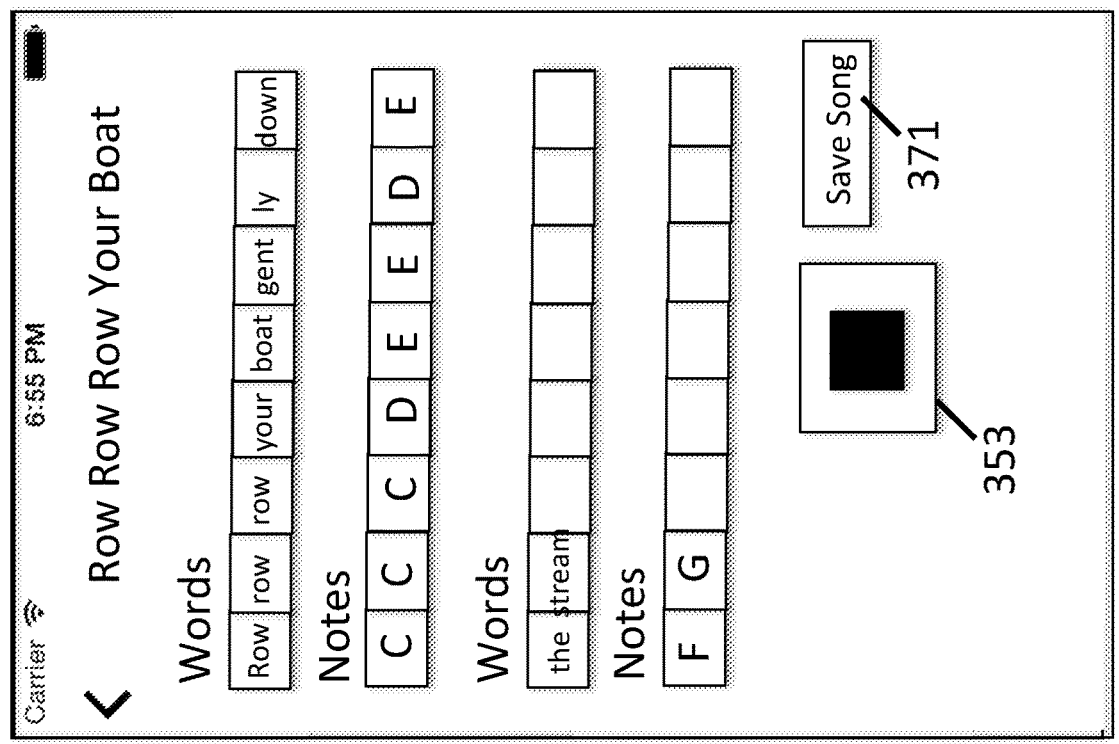
FIGS. 25a-25b illustrate an embodiment of a user interface for inputting music into the system.

In some embodiments, users may program and store songs on their own. By defining a simple application programming interface (API), users may share and download songs. In some cases, the songs may be comprised of multiple pages and the songs may be in different languages. FIG. 25a illustrates an embodiment of a programmable song input user interface. The user can input the notes into the notes spaces and the corresponding words into the words spaces. Once a portion of a song or a complete song has been input through the user interface, the user may press the "Save Song" button 371 to store the song in memory. The user may then be able to recall the song from memory and play the song or use the user interface to edit the songs.

Figure 25B:
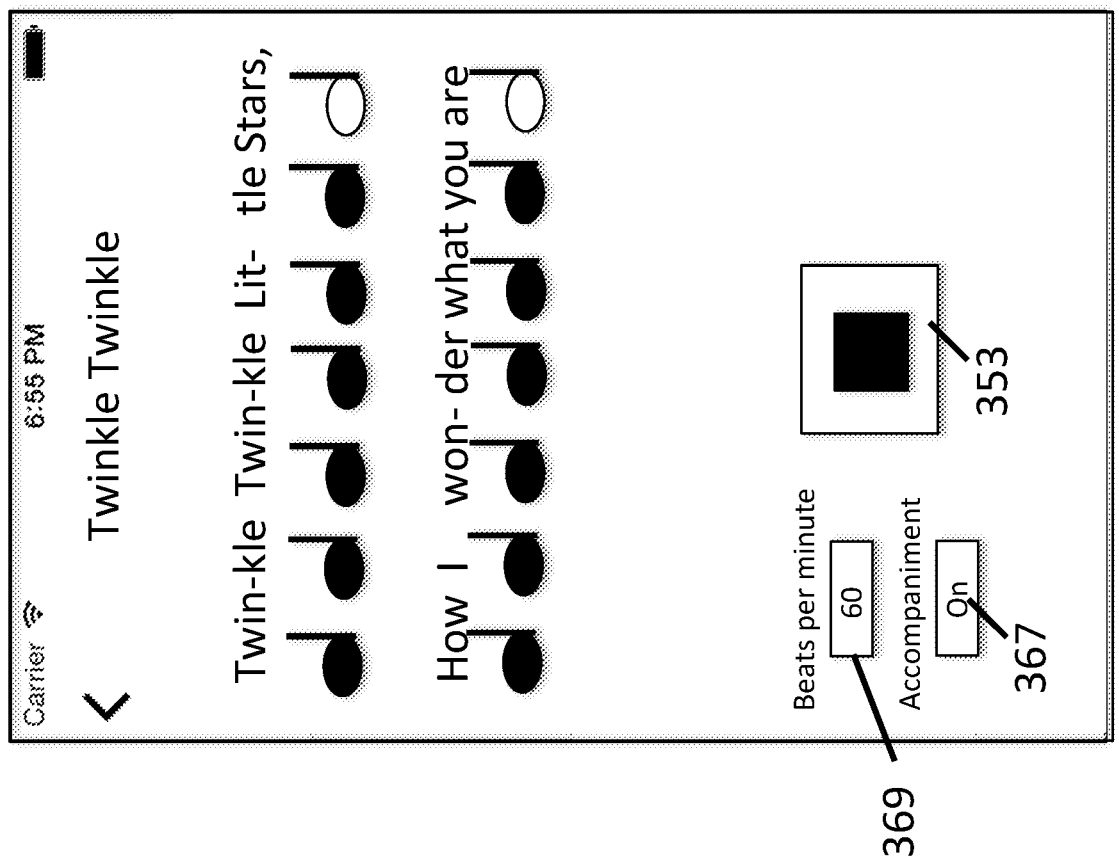

With reference to FIG. 25b, in an embodiment the user interface may also allow the user to control the playback speed of the stored songs. For example, in an embodiment the user interface can allow the user to control the "Beats per minute" 369 which may be selected by the user to set the duration of a quarter note. The "Beats per minute" control may turn on a metronome or other rhythm device to sound. In this example, the user has set 60 beats per minute. The user interface may also allow a background "Accompaniment" to be played while the user controls the timing and duration of the notes by engaging or contracting their core. The user will have the option of having the accompaniment on or off by actuating the accompaniment button 367.

Figure 26:
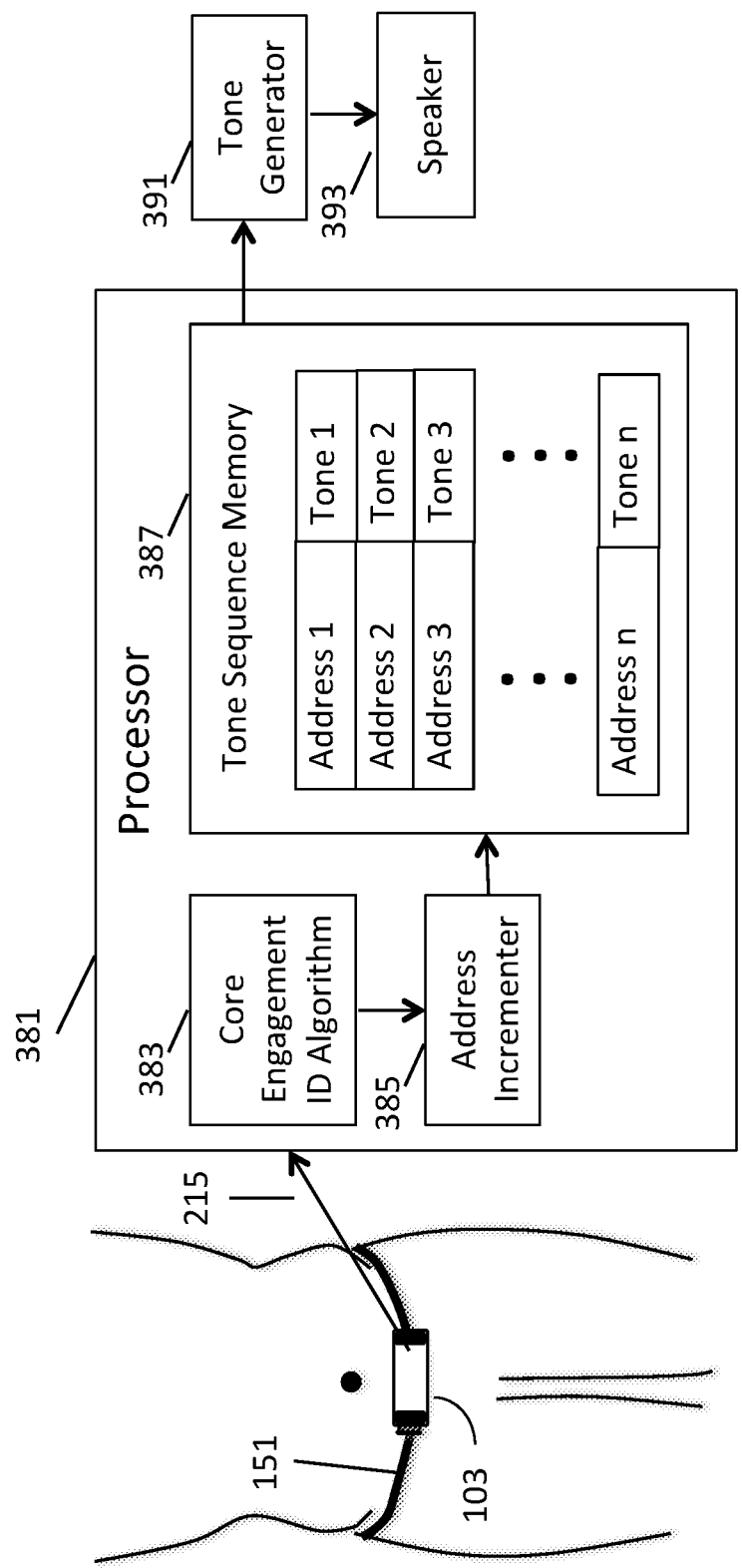
FIG. 26 illustrates the system high level structure from the wearable device, to the program running on the processor, to the tone generator and speaker.

With reference to FIG. 26, a high level block diagram is shown with wearable device 103 on a user's core. Core contraction sensor data 215 is input to the Core Engagement Identification Algorithm 383. From the Algorithm 383, core_engaging 212 and core_disengaging 214 or core relaxed 203 and engaged 205 data may be passed to Address Incrementer 385. Tones or notes to a song may be programmed into the Tone Sequence Memory 387. As the user engages the core muscles, and core_engaging 214 or engaging 205 signals to the Address Incrementer 385, tones or notes in the Tone Sequence Memory 387 may be passed with each subsequent core engagement to the Tone Generator 391 and played through the Speaker 393. Core Engagement Identification Algorithm 383, Address Incrementer 385, and Tone Sequence Memory 387 are shown running on Processor 381. In an embodiment, a portion of the algorithm may be run on the processor on wearable device 103, while a portion of the algorithm may be run on the processor in the smart device. Tone Generator 391 and Speaker 393 may be on the smart device.

Figure 27:
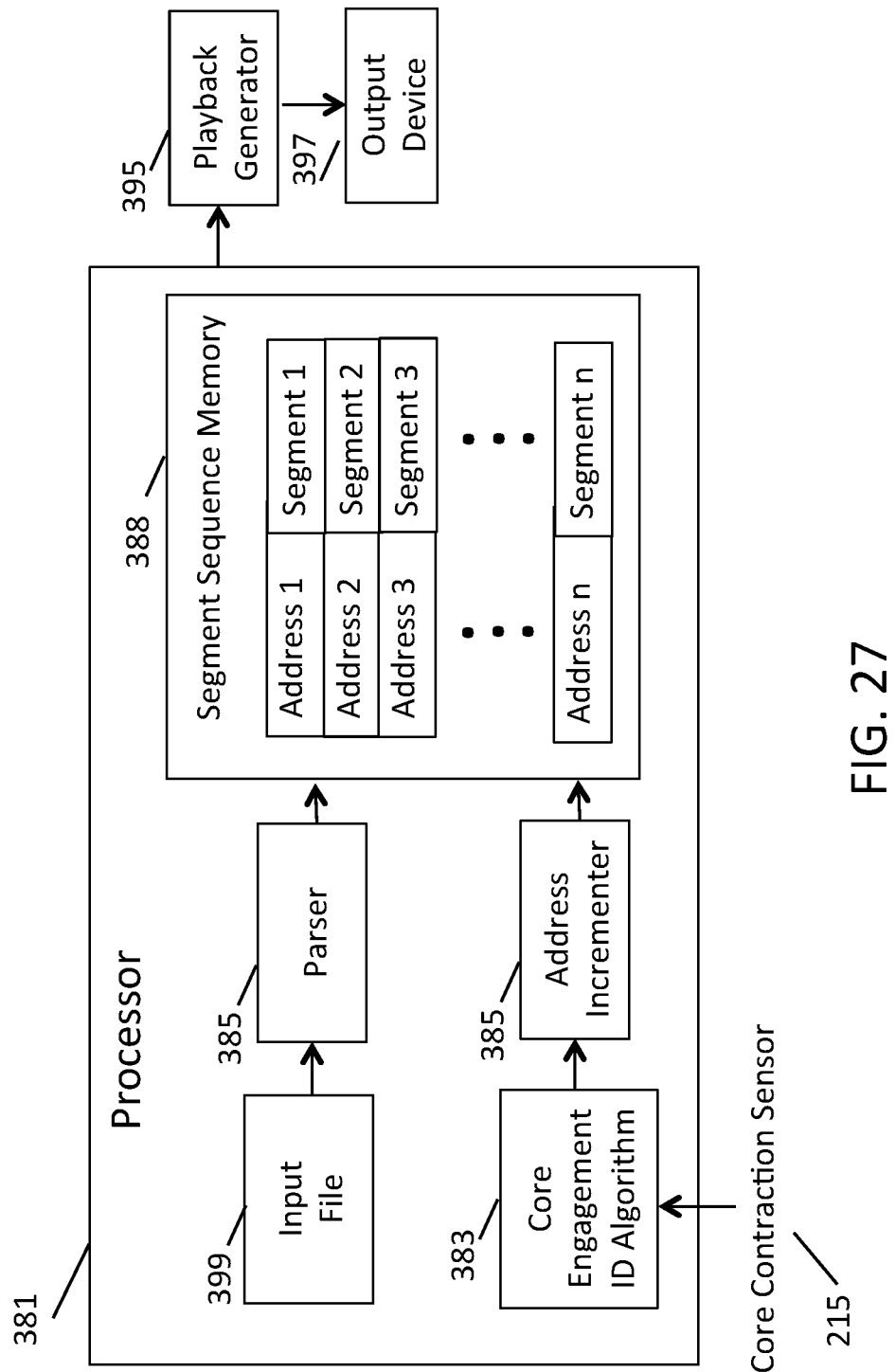
FIG. 27 illustrates a general structure that takes a data file and generates data segments that may be played sequentially on successive core engagements.

With reference to FIG. 27, an Input File 399 containing words to a document, pledge, or creed, or recorded audio, or recorded video, or other data may be input to a Parser 385 that separates the words, recorded audio, recorded video, or other data into a sequence of word segments, audio segments, video segments, or other data segments, and stores this segmented data into a Segment Sequence Memory 388 with sequenced addresses. Data from the Core Contraction Sensor 215 from the wearable device 103 is input the Core Engagement Identification Algorithm 383. From the Algorithm 383, core_engaging 212 and core_disengaging 214 or core relaxed 203 and engaged 205 data may be passed to Address Incrementer 385. As the user engages the core muscles, and core_engaging 214 or engaging 205 signals to the Address Incrementer 385, a data segment in the Segment Sequence Memory 388 may be passed with each subsequent core engagement to the Playback Generator 395 and played through the Output Device 393. Output Device 393 may include a speaker and a display for playing back audio and video. Playback Generator 395 generates audio and video signals as appropriate. Data in the Segment Sequence Memory 388 may be compressed or uncompressed digital samples or words that undergo text to speech conversion, or other data formats that may be converted to sound or video. While one Processor 381 is shown in the figure, more than one processor may be utilized in an embodiment. In an embodiment, a portion of the algorithm may be run on the processor on wearable device 103, while a portion of the algorithm may be run on the processor in the smart device. In an embodiment, Playback Generator 391 and Output Device 393 may be on the smart device.

In an embodiment the app can be configured to emit a variable tone when the core is contracted, the system can effectively allow the Core to be used as a Musical Instrument. This aspect of the invention is somewhat akin to whistling. In an embodiment, the user controlled intensity of the core contraction or core engagement is mapped or adjusted into a pitch. The pitch of the sounded note is dependent upon the intensity of the engagement. The intensity of the engagement may be identified or sensed by the wearable device. Both bracing and hollowing may be supported to adjust the pitch of the tone output. In the case of hollowing, a lower intensity sensed by the wearable device may result in a higher sounded pitch. The mapping of the intensity of the core contraction or core engagement into a pitch may be linear or non-linear. A button on the smart device running the app may define when the note is sounded or when sound should be suspended. The user may be focused on modulating the intensity of their core so pauses may be implemented by pushing a button or icon on the app instead of the user relaxing their core muscles.

In other embodiments, the processor can be coupled to a microphone which can identify songs played by other music sources. The App can use a song identifying program such as: Shazam, TrackID, Soundhound, MusiXmatch and Spotsearch. Based upon the song's identification, the app can obtain the tones and notes associated with the song and compare the core contractions with the tones or notes of the song. The processor can score each song based upon the number of coordinated core contractions to tones in the song.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing core contraction procedural memory, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A method for development a core muscle, comprising:
providing a contraction sensor in a wearable device with a bumper extending from the wearable device which is pressed against an abdomen of a user with a belt and a microphone in communication with a processor, wherein the contraction sensor detects pressure from the bumper;
adjusting a tension on the belt to adjust the bumper against the abdomen of the user based upon core contraction signals and core relaxation signals which are detected by the contraction sensor, the core contraction signal and the core relaxation signal are transmitted to the processor and displayed on the visual display;
detecting ambient musical notes by the microphone coupled to the processor;
detecting core contractions of the user with the contraction sensor;
transmitting core contraction signals from the contraction sensor to the processor;
detecting by the processor, a timing relationship between the core contractions and the ambient musical tones detected by the microphone;
analyzing the timing relationship by the processor to determine if the core contractions correspond to the ambient musical tones detected by the microphone;
outputting by the processor correct signals for each of the core contractions that correspond to the ambient musical tones; and
outputting by the processor error signals for each of the core contractions that do not correspond to the ambient musical tones.

2. The method of claim 1 wherein the core contractions are detected when the force applied to the core contraction sensor exceeds a predetermined contraction force.

3. The method of claim 1 wherein the core contractions correspond to the ambient musical tones when the core contractions are within 0.1 second of the ambient musical tones.

4. The method of claim 1 further comprising:
providing a memory coupled to the processor wherein songs having a sequence of the ambient musical tones are stored in the memory.

5. The method of claim 1 further comprising:
providing a memory coupled to the processor;
determining durations of the ambient musical tones that is optimized for the user; and
storing the duration of time that is optimized for the user in the memory.

6. The method of claim 1 further comprising:
providing a graphical user interface displayed on a visual display coupled to the processor; and displaying a score based upon the correct signals and the error signals on the visual display.

7. A method for development a core muscle, comprising:
providing a contraction sensor in a wearable device with a bumper extending from the wearable device which is pressed against an abdomen of a user with a belt and a microphone in communication with a processor which is coupled to a visual display, wherein the contraction sensor detects pressure from the bumper;
adjusting a tension on the belt to adjust the bumper against the abdomen of the user based upon core contraction signals and core relaxation signals which are detected by the contraction sensor, the core contraction signal and the core relaxation signal are transmitted to the processor and displayed on the visual display;
detecting ambient musical tones from the microphone coupled to the processor;
detecting core contractions of the user with the contraction sensor;
transmitting core contraction signals from the contraction sensor to the processor;
detecting by the processor, a timing relationship between the core contractions and the ambient musical tones detected by the microphone;
analyzing the timing relationship by the processor to determine if the core contractions correspond to the ambient musical tones detected by the microphone;
outputting by the processor a correct signals for each of the core contractions that correspond to the ambient musical tones; and
outputting by the processor error signals for each of the core contractions that do not correspond to the ambient musical tones.

8. The method of claim 7 wherein the core contractions are detected when the force applied to the core contraction sensor exceeds a predetermined contraction force.

9. The method of claim 7 further comprising:
providing a graphical user interface displayed on a visual display coupled to the processor; and
displaying visual tones on the visual display that correspond to the ambient musical tones detected from the microphone.

10. The method of claim 7 wherein the core contractions correspond to the ambient musical tones when the core contractions are within 0.1 second of the ambient musical tones.

11. The method of claim 7 further comprising:
providing a memory coupled to the processor wherein songs having a sequence of the ambient music tones are stored in the memory.

12. The method of claim 7 further comprising:
providing a memory coupled to the processor;
determining durations of the ambient musical tones that is optimized for the user; and
storing the duration of time that is optimized for the user in the memory.

13. The method of claim 7 further comprising:
providing a graphical user interface displayed on a visual display coupled to the processor; and
displaying a score based upon the correct signals and the error signals on the visual display.

14. A method for development a core muscle, comprising:
providing a contraction sensor in a wearable device with a bumper extending from the wearable device which is pressed against an abdomen of a user with a belt, a microphone, and a processor in communication with the contraction sensor and the microphone, wherein the contraction sensor detects pressure from the bumper and the microphone detects ambient musical tones;
adjusting a tension on the belt to adjust the bumper against the abdomen of the user based upon core contraction signals and core relaxation signals which are detected by the contraction sensor, the core contraction signal and the core relaxation signal are transmitted to the processor and displayed on the visual display;
detecting core contractions of the user with the contraction sensor;
transmitting the core contraction signals from the contraction sensor to the processor;
detecting the ambient musical notes by the microphone coupled to the processor;
detecting by the processor, a timing relationship between the core contractions and the ambient musical tones;
analyzing the timing relationship by the processor to determine if the core contractions correspond to the ambient musical tones detected by the microphone;
outputting by the processor correct signals for each of the core contractions that correspond to the ambient musical tones; and
outputting by the processor error signals for each of the core contractions that do not correspond to the ambient musical tones.

15. The method of claim 14 wherein the ambient musical notes are emitted for a predetermined duration.

16. The method of claim 14 wherein the tone is the ambient musical notes are emitted by an instrument.

17. The method of claim 14 wherein the ambient musical notes are emitted by at least one of: a voice, a piano, a guitar, a flute, a saxophone, a trumpet, or a violin.

18. The method of claim 14 wherein the ambient musical notes are two or more songs.

* * * * *